United States Patent [19]

Nadler et al.

[11] Patent Number: 5,051,417
[45] Date of Patent: Sep. 24, 1991

[54] INDOLYTHIADIAZINES FOR TREATING HEART FAILURE

[75] Inventors: Guy Nadler; Michel Martin; Richard Zimmermann, all of Saint Gregoie, France

[73] Assignee: Les Laboratoires Beecham S.A., France

[21] Appl. No.: 379,626

[22] Filed: Jul. 13, 1989

[30] Foreign Application Priority Data

Jul. 15, 1988 [GB] United Kingdom ............... 8816944

[51] Int. Cl.$^5$ .................... C07D 285/16; A61K 31/54
[52] U.S. Cl. .................................... 514/222.5; 544/6; 544/8
[58] Field of Search ................. 544/6, 8, 68, 182, 230; 514/222.5

[56] References Cited

U.S. PATENT DOCUMENTS 4,678,785  7/1987  Ao et al. ............................. 514/222
4,774,238  9/1988  Broom et al. ....................... 514/192

FOREIGN PATENT DOCUMENTS 0161918  11/1985  European Pat. Off. .
0259871  3/1988  European Pat. Off. .
0303418  2/1989  European Pat. Off. .

OTHER PUBLICATIONS

Hodges et al. "Chemical and Biological" CA 69:43883g (1968).
Walker et al. "Synthesis of New 3 . . ." CA 63:11563h (1965).
Youngdale et al. "Synthesis and Phamacological . . ." CA 61:11957e (1964).
Robertson et al., "Dihydro Pyridazinone Cardiotonics : Synthesis and Intropic Activity of S'-(1,4,5,6-Tetrahydro-6-oxo-3-Pyridazinyl) Spiro [Cycloalkane-1,-3'-[3H] Indol]-2'(1'H)-Ones," J. Med. Chem. 1987 (30) 824-829.

Primary Examiner—Alan L. Rotman
Assistant Examiner—Celia Chang
Attorney, Agent, or Firm—Rosen & Colin

[57] ABSTRACT

A compound of formula (I) or a pharmaceutically acceptable salt thereof, in which,
$R_1$ is hydrogen or lower alkyl;
$R_2$ is hydrogen or lower alkyl;
$R_4$ and $R_4'$ together form a group =N—Ra, or =CRaRb, where Ra is hydrogen, lower alkyl, aryl, aryloxy, lower alkylcarbonyl, arylcarbonyl, aryloxycarbonyl, lower alkoxy, lower alkoxy carbonyl, lower alkoxy carbonyl alkoxy, lower thioalkoxy, hydroxy, nitrile, heterocyclyl, or —NRcRd, where Rc is hydrogen, lower alkyl, cycloalkyl, aryl, aralkyl, lower alkylcarbonyl, arylcarbonyl, aminocarbonyl, aminothiocarbonyl, aminoiminocarbonyl, lower alkoxycarbonyl, lower alkoxythiocarbonyl, aryloxycarbonyl, thiocarbonyl, nitrile, carboxyl, heterocyclyl or heterocyclylcarbonyl, and Rd is hydrogen or lower alkyl; Rb is hydrogen, lower alkyl, aryl, lower alkylcarbonyl, lower alkoxycarbonyl, nitrile or nitro;
or $R_4$ is —NH—Ra, in which Ra is as defined above, and $R_4'$ is hydrogen or lower alkyl;
each of $R_3$ and $R_5$ is independently hydrogen, lower alkyl, aryl, lower alkylcarbonyl, arylcarbonyl, aralkylcarbonyl, heterocyclylcarbonyl, optionally substituted aminocarbonyl, lower alkoxycarbonyl or aryloxycarbonyl;
$R_6$ is hydrogen, lower alkyl or halogen; and A is sulphur, oxygen, —NH— or —CH$_2$—, is useful for the treatment of heart disease.

7 Claims, No Drawings

INDOLYTHIADIAZINES FOR TREATING HEART FAILURE

This invention relates to compounds having pharmacological activity, pharmaceutical compositions containing them, processes for their preparation, and their use as active therapeutic agents, particularly in the treatment of acute or chronic heart disease.

EP-A-0052442 discloses phenyl-thiadiazinone, oxadiazinone or triazinone derivatives which are phosphodiesterase inhibitors and are said to possess cardiotonic properties. There is no disclosure in this document of the derivatives having the property of increasing the sensitivity of myocardial contractile proteins to calcium, which is believed to be an additional, useful mechanism of action for cardiotonic agents.

It has now been discovered that certain novel phenyl-thiadiazinone oxadiazinone and triazinone derivatives in which the phenyl nucleus forms part of a substituted 2-oxo-2,3-dihydroindole ring are phosphodiesterase inhibitors, and some of these derivatives may also increase the sensitivity of myocardial contractile proteins to calcium. The novel derivatives are therefore potentially valuable drugs in the treatment of congestive heart failure.

According to the present invention there is provided a compound of formula (I), or a pharmaceutically acceptable salt thereof:

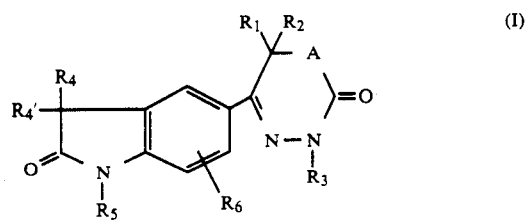

in which, $R_1$ is hydrogen or lower alkyl;

$R_2$ is hydrogen or lower alkyl;

$R_4$ and $R_4'$ together form a group =N—Ra, or =CRaRb, where Ra is hydrogen, lower alkyl, aryl, aryloxy, lower alkylcarbonyl, arylcarbonyl, aryloxycarbonyl, lower alkoxy, lower alkoxy carbonyl, lower alkoxy carbonyl alkoxy, lower—thioalkoxy, hydroxy, nitrile, heterocyclyl, or —NRcRd, where Rc is hydrogen, lower alkyl, cycloalkyl, aryl, aralkyl, lower alkylcarbonyl, arylcarbonyl, aminocarbonyl, aminothiocarbonyl, aminoiminocarbonyl, lower alkoxycarbonyl, lower alkoxythiocarbonyl, aryloxycarbonyl, thiocarbonyl, nitrile, carboxyl, heterocyclyl or heterocyclylcarbonyl, and Rd is hydrogen or lower alkyl; Rb is hydrogen, lower alkyl, aryl, lower alkylcarbonyl, lower alkoxycarbonyl, nitrile or nitro;

or $R_4$ is —NH—Ra, in which Ra is as defined above, and $R_4'$ is hydrogen or lower alkyl;

Each of $R_3$ and $R_5$ is independently hydrogen, lower alkyl, aryl, lower alkylcarbonyl, arylcarbonyl, aralkylcarbonyl, heterocyclylcarbonyl, optionally substituted aminocarbonyl, lower alkoxycarbonyl or aryloxycarbonyl;

$R_6$ is hydrogen, lower alkyl or halogen; and A is sulphur, oxygen, —NH—or —CH$_2$—.

The terms 'lower alkyl' and 'lower alkoxy' are used herein to mean straight or branched chain alkyl and alkoxy groups having up to 6, preferably up to 4, carbon atoms.

The term 'cycloalkyl' is used herein to mean a single optionally substituted ring having up to 12 carbon atoms in the ring.

The term 'aryl' is used herein to include optionally substituted carbocyclic aromatic groups, preferably having single or fused rings with 6 to 12 ring carbon atoms. Examples are phenyl and substituted phenyl. Examples of substituents are one or more atoms or moieties selected from amino, nitro, hydroxyl, lower alkyl, lower alkoxy, halogen, trifluoromethyl, lower alkyl sulphonyl and carboxyl, and they may be located in any position on the aromatic ring system.

The term 'aralkyl' is used herein to include aryl groups, as defined above, linked to an alkylene group which suitably contains from 1 to 6 carbon atoms. The alkylene group may itself be optionally substituted by, for example, a further aryl group. Examples are benzyl and substituted benzyl.

The term 'heterocyclyl' is used herein to include optionally substituted single or fused ring systems having 5 to 12 ring atoms, and comprising up to four hetero-atoms in the or each ring selected from oxygen, nitrogen and sulphur. The ring system may be aromatic or non aromatic, and examples are pyridyl, thienyl or imidazolyl.

In a preferred group of compounds of formula (I), each of $R_1$, $R_2$, $R_3$, $R_5$ and $R_6$ is independently hydrogen or lower alkyl, particularly methyl, and A represents sulphur.

The compounds of the invention have two potential chiral centres at the $R_4/R_4'$ and $R_1/R_2$ substituted positions, and can therefore exist in more than one stereoisomeric form. The invention extends to all such forms and to mixtures thereof, including all enantiomers, diastereomers, and racemates.

The pharmaceutically acceptable salts of the compounds of formula (I), (when the compound contains a salifiable group) include acid addition salts with conventional acids such as hydrochloric, hydrobromic, boric, phosphoric, sulphuric and pharmaceutically acceptable organic acids such as acetic, tartaric, maleic, citric, succinic, benzoic, ascorbic, methanesulphonic, c-keto-glutaric, c-glycerophosphoric, and glucose-1-phosphoric acids. Preferably the acid addition salt is a hydrochloride.

The compounds of the formula (I) and their pharmaceutically acceptable salts may also form solvates with pharmaceutically acceptable solvents, and such solvates are included within the expression 'a compound of formula (I)' used herein.

Salts of the compounds of the formula (I) which are not pharmaceutically acceptable may be useful as intermediates in the preparation of pharmaceutically acceptable salts of compounds of the formula (I) or the compounds of the formula (I) themselves, and as such form an aspect of the present invention.

According to a further aspect of the invention, the compounds of formula (I) may be prepared by treating a compound of formula (II)

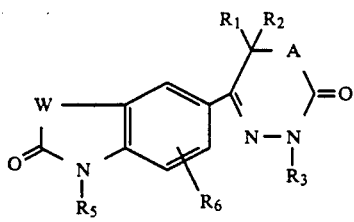

(II)

in which $R_1$, $R_2$, $R_3$, $R_5$, $R_6$ and A are as defined in formula (I) and W represents —$CH_2$— or

(a) when W represents

with a compound of formula (III)

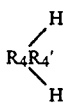

(III)

in which $R_4R_4'$ represents >N—$R_a$, >$CHR_a$ or >$CR_aR_b$ as defined in claim 1, or (b) when W represents —$CH_2$—, with a compound of formula (IV)

(IV)

where $R_4$ and $R_4'$ are =N—Ra or =$CR_aR_b$ as defined in formula (I), or with a diazonium salt containing an anion of formula (V)

(V)

where Rc is as defined in formula (I),
and thereafter if desired converting a compound of formula (I) thereby produced to a pharmaceutically acceptable salt thereof or to a further compound of formula (I).

The reaction is preferably carried out in an organic solvent, for example ethanol, and in the presence of a base, such as potassium carbonate or sodium hydroxide. The reaction preferably occurs at between room temperature and the boiling point of the solvent, and for a period of from about 15 minutes to 3 hours.

The compounds of formula (I) may be converted into pharmaceutically acceptable salts in conventional manner by, for example, treatment with an appropriate acid.

Certain compounds of formula (I) may be converted to other compounds of formula (I) in accordance with known methods. For example, compounds of formula (I) in which $R_4$ and $R_4'$ together represent =N—$R_a$ may be converted to compounds in which $R_4$ is —NH—$R_a$ and $R_4'$ is hydrogen by reduction using zinc in acetic acid.

Generally speaking, it has been found that the latter compounds tend to be unstable, reverting to the unsaturated starting materials in the presence of air. However, the compounds can usually be stabilised by converting them to a salt form.

A particularly preferred, and novel, process for converting a compound of formula (I) to another compound of formula (I) comprises treating a compound of formula (Ia)

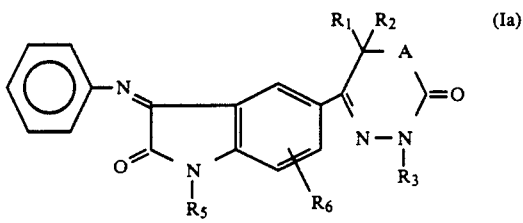

(Ia)

in which $R_1$, $R_2$, $R_3$, $R_5$, $R_6$ and A are as defined in formula (I), with a compound of formula (Va)

Ra—$NH_2$ (Va)

in which Ra is as defined in formula (I), to form a compound of formula (I) in which $R_4$ and $R_4'$ are together the group =N—Ra.

The compounds of formula (II) in which W is

may themselves be prepared by oxidising a compound of formula (IIa)

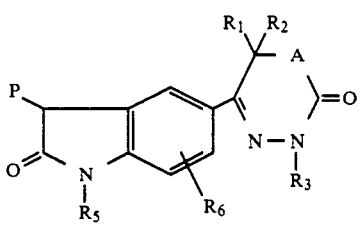

(IIa)

in which $R_1$, $R_2$, $R_5$, $R_6$ and A are as defined in formula (I) and P is an oxidisable protecting group, such as thioalkyl, particularly thiomethyl.

The compounds of formula (IIa) in which A is sulphur may themselves be prepared by treating a compound of formula (VI)

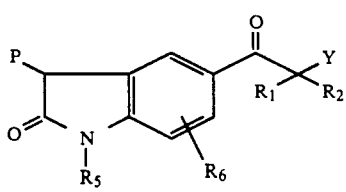

(VI)

in which $R_1$, $R_2$, $R_5$ and $R_6$ are as defined in formula (I), P is as defined in formula (IIa), and Y is a leaving group, with a compound of formula (VII)

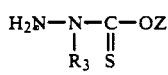

(VII)

in which $R_3$ is as defined in formula (I), and Z is an alkyl group, preferably $C_{1-6}$ alkyl, for example methyl ethyl or tertiarybutyl, or an ammonium or alkali metal ion.

Y is preferably a halogen atom, an alkanesulphonyloxy group (such as methylsulphonyloxy) or arylsulphonyloxy (such as benzenesulphonyloxy or p-toluenesulphonyloxy).

The reaction is preferably carried out in an organic solvent, for example ethanol, acetonitrile or dimethylformamide, at between room temperature and the boiling point of the solvent. The reaction time may be decreased by employing a catalyst such as trifluoroacetic acid or triethylamine.

The compounds of formula (IIa) in which W is

and A is oxygen may be prepared by cyclising a compound of formula (VIII):

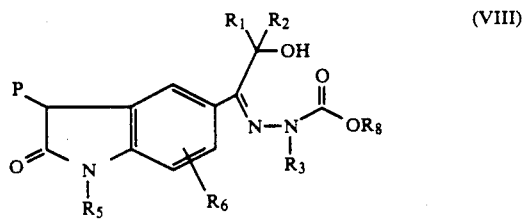

in which $R_1$, $R_2$, $R_3$, $R_5$ and $R_6$ are as defined in formula (I), P is as defined in formula (IIa), and R8 is an alkyl group, preferably $C_{1-6}$ alkyl such as methyl or ethyl. The cyclisation may be carried out in the presence of a base, such as sodium ethoxide, in a diluent or solvent, such as ethanol at about ambient temperature.

The compounds of formula (IIa) in whioh W is

and A is —NH— may be prepared by treating a compound of formula (IX):

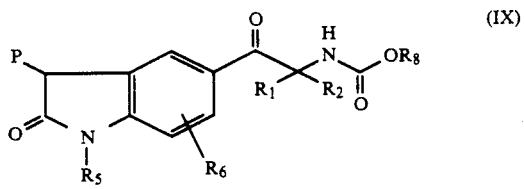

in which $R_1$, $R_2$, $R_5$ and $R_6$ are as defined in formula (I), P is as defined in formula (IIa), and $R_8$ is as defined in formula (VIII) with a compound of formula (X):

H₂N—NH—R₃       (X)

in which $R_3$ is as defined in formula (I).

The reaction may be carried out in a diluent or solvent, such as ethanol, and suitably at a temperature up to the boiling point of the diluent or solvent.

The compounds of formula (VI) may themselves be prepared by treating a compound of formula (XI)

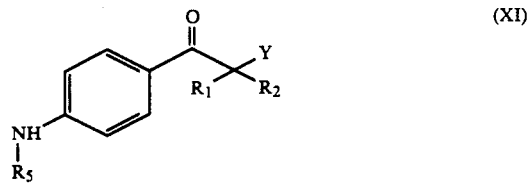

in which $R_1$, $R_2$, $R_5$ and Y are as defined in formula (VI) with a compound of formula (XIa)

P.CH₂COOR₉       (XIa)

in which P is as defined in formula (IIa) and $R_9$ is an alkyl group, preferably $C_{1-6}$ alkyl.

The compounds of formula (XI) are known compounds (Kulkarni et al., J. Pharm. Sci., 58, (7) 852–7, 1969) or can be made from these known compounds by known methods.

The compounds of formula (XIa) are known compounds or are preparable in analogous manner to the known compounds of formula (XIa).

The compounds of formulae (VII) are known compounds, or are preparable in analogous manner to the known compounds of formula (VII).

Compounds of formula (VIII) may be prepared by treating a compound of formula (XII):

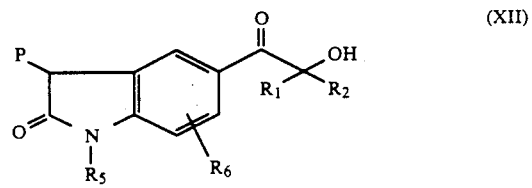

in which $R_1$, $R_2$, $R_5$ and $R_6$ are as defined in formula (I) and P is as defined in formula (IIa), with an alkyl carbazate of formula (XIII):

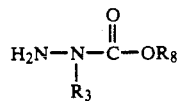

in which $R_3$ and $R_8$ are as defined in formula (VIII).

Compounds of formula (XII) may themselves be prepared by hydrolysing a compound of formula (VI).

Compounds of formula (IX) may be prepared by treating a compound of formula (XIV):

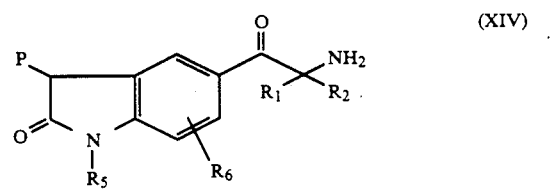

in which $R_1$, $R_2$, $R_5$ and $R_6$ are as defined in formula (I) and P is as defined in formula (IIa), with a compound of formula (XV):

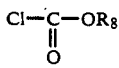

in which $R_8$ is as defined in formula (VIII).

Compounds of formula (XIV) may themselves be prepared by treating a compound of formula (VI) with sodium azide, and reducing the thus formed azide with hydrogen in the presence of a palladium/charcoal catalyst.

Compounds of formula (X), (XIII) and (XV) are known compounds, or can be prepared from known compounds by known methods.

Intermediate compounds of formula (II) in which W is

are disclosed in EP-A-0303418, and some of those in which W is —CH$_2$— are generically disclosed in EP-A-0052442.

In general, compounds of formula (II) in which W is —CH$_2$— may be prepared in an analogous manner to similar compounds which are disclosed in EP-A-0303418 and EP-A-0052442.

In order to utilise the potential cardiotonic activity of the compounds of formula (I) the invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate.

Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved.

Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

In addition such compositions may contain further active agents such as vasodilator agents and diuretics.

As is common practice, the compositions will usually be accompanied by written or printed directions for use in the medical treatment concerned.

The invention further provides a method of treatment or prophylaxis of heart disease in mammals, such as humans, which comprises the administration of an effective amount of a compound of formula (I), or a pharmaceutically acceptable salt thereof, to the sufferer.

An amount effective to treat the disorders hereinbefore described depends on the relative efficacies of the compounds of the formula (I), the nature and severity of the disorders being treated and the weight of the mammal. However, a unit dose may contain from 1 to 1,000 mg, normally from 1 to 100 mg, for example 2 to 50 mg, of the compound of the invention. Unit doses will normally be administered once or more than once a day, for example 2,3,4,5 or 6 times a day, more usually 2 to 4 times a day, such that the total daily dose is normally in the range, for a 70 kg adult of 1.0 to 2500 mg, more usually 50 to 2000 mg, for example 10 to 75 mg, that is in the range of approximately 0.002 to 35 mg/kg/day, more usually 1 to 30 mg/kg/day, for example 0.15 to 1 mg/kg/day.

In an additional aspect of the invention there is provided a compound of formula (I) or a pharmaceutically acceptable salt thereof, for use as an active therapeutic substance, and in particular for the treatment of heart disease.

Furthermore, the invention provides the use of a compound of formula (I) or a pharmaceutically acceptable salt thereof in the manufacture of a medicament for the treatment of heart disease.

The following examples illustrate the preparation of compounds of the invention, the descriptions illustrate the preparation of intermediates, and the pharmacological data illustrate the activity of the compounds of the invention.

DESCRIPTION 1

5-(3,6-Dihydro-6-methyl-2-oxo-2H-1,3,4-thiadiazin-5-yl)-1,3-dihydro-3,3-dimethyl-2H-indol-2-one

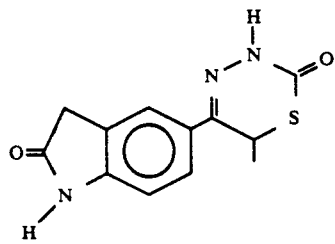
(D1)

A mixture of 38 g (0.142mol) 5-(2-bromo-1-oxopropyl)-1,3-dihydro-2H-indol-2-one, 15.04 g (0.142mol) methoxy thiocarbonylhydrazine (K. A. Jensen, U. Anthoni, A. Holm, Acta. Chem. Scand., 23,1916,1969) in 815 ml acetonitrile was refluxed under stirring for 6.5 hours. After cooling in ice, the crude crystalline product was collected, washed with acetonitrile (2x50 ml) and dried to give 15.23 g of white crystals.

Yield : 41%.

m.p. : 270° C.

IR (KBr): $\nu$=3,450; 3,200; 1,690; 1,640; 1,615; 1,495; 1,250; 1,200 cm$^{-1}$.

NMR (DMSO—d$_6$): $\delta$=1.47 ppm (d,J=7.1 Hz,3H,CH$_3$CH); 3.54 (s,2H,CH$_2$CO); 4.70 (q,J=7.1 Hz,1H,CHCH$_3$); 6.89 (d,J=7.9 Hz, 1H,Ar); 7.66 (d,J=7.9 Hz,1H,Ar); 7.68 (s,1H,Ar); 10.63 (s,1H,exch.-D$_2$O,NH); 11.60 (s,1H, exch.D$_2$O,NH).

EXAMPLE 1

1,3-Dihydro-5-(3,6-dihydro-6-methyl-2-oxo-2H-1,3,4-thiadiazin-5-yl)-3-hydroxyimino-2H-indol-2-one

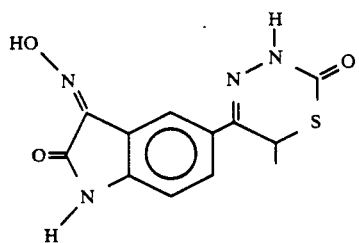
(E1)

A mixture of 2 g (7.3mmol) 1,3 dihydro-5-(3,6-dihydro-6-methyl-2-oxo-2H-1,3,4-thiadiazin-5-yl)-3H-indole-2,3 (1H)-dione, 0.5 g (7.3mmol) hydroxylamine hydrochloride, 1 g (7.3mmol) potassium carbonate and 50 ml ethanol were refluxed for 2 hours. Yellow crystals were filtered off, triturated in water and dried under vacuum. Another crop of yellow crystals were obtained by adding water to the filtrate.

Yield: 34%.

m.p.: 170° C.

IR (KBr): $\nu$=3,200 (large); 1,725; 1,640; 1,615; 1,235 cm$^{-1}$.

NMR (DMSO—d$_6$): $\delta$=1.47 (d,J=7.1 Hz,3H,CH$_3$—CH); 4.71 (q,J=7.1 Hz,1H,CH$_3$—CH); 6.96 (d,J=8.3Hz,1H,Ar); 7.80 (d,J'=8.3 Hz,1H,Ar); 8.47 (s,1H,Ar); 10.97 (s,1H,exch.D$_2$O,NH) 11.63 (s,1H,exch.D$_2$O,NH). (Multisolv):=1,54 (d,J=7.2 Hz,3H,CH$_3$—CH); 4.53 (q,J=7.2 Hz, 1H,CH$_3$—CH); 6.93 (d,J=8.2 Hz,1H,Ar); 7.75 (dd,J=8.2 Hz, J'=1.7 Hz,1H,Ar); 8.48 (d,J=1.4 Hz,1H,Ar); 10.83 (s,1H, exch.D$_2$O,NH); 11.49 (s,1H,exch.D$_2$O,NH); 13.34 (s,1H,exch.D$_2$O,OH).

EXAMPLE 2

1,3-Dihydro-5-(3,6-dihydro-6-methyl-2-oxo-2H,1,3,4 thiadiazin-5-yl)-3-methoxyimino-2H-indol-2-one

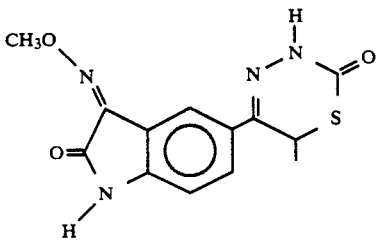
(E2)

Starting from 1,3-dihydro-5-(3,6-dihydro-6-methyl-2-oxo-2H-1,3,4 thiadiazin-5-yl)-3H-indole-2,3 (1H)-dione and methoxylamine and following the method described in example 1, afforded the desired compound.

Yield: 62%.

m.p.: 290° C.

IR (KBr): $\nu$=3,300; 1,745; 1,718; 1,615; 1,585; 1,295; 1,080; 1,025 cm$^{-1}$.

NMR (DMSO—d$_6$): $\delta$=1.48 (d,J=7.1 Hz,3H,CH$_3$CH); 4.23 (s,3H, CH$_3$O); 4.72 (q,J=7.1 Hz,1H,CH$_3$—CH); 6.98 (d,J=8.2 Hz,1H,Ar); 7.84 (dd,J=8.2 Hz,J'=1.5 Hz,1H,Ar); 8.30 (d,J'=1.5 Hz,1H,Ar); 11.07 (s,1H,exch.D$_2$O,NH); 11.68 (s,1H,exch.D$_2$O,NH).

EXAMPLE 3

O-Methyl 2-[2,3-dihydro-5-(3,6-dihydro-6-methyl-2-oxo-2H-1,3,4-thiadiazin-5-yl)-2-oxo-1H-indol-3-ylidene]-hydrazine carbothioate

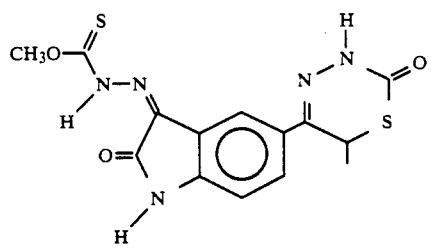
(E3)

A mixture of 1g (3.6mmol) 1,3-dihydro-5-(3,6-dihydro-6-methyl-2-oxo-2H-1,3,4-thiadiazin-5-yl)-3H-indole-2,3 (1H)-dione, 0.38 g (3.6mmol) methoxythiocarbonyl hydrazine in 30 ml ethanol were refluxed for 30 minutes. After cooling, filtration afforded the desired compound.

Yield: 71% (950 mg). orange crystals.

m.p.: 245° C.

IR (KBr): $\nu$=3,200; 3,150; 1,700; 1,650; 1,620; 1,490; 1,450; 1,305; 1,220; 1,155 cm$^{-1}$.

NMR (DMSO—d$_6$): $\delta$=1.47 ppm (d,J=7.1 Hz,3H,CH$_3$CH); 4.17 (s,3H,CH$_3$O); 4.83 (q,J=7.1 Hz,1H,CH$_3$—CH); 7.03 (d,J=8.3 Hz,1H,Ar); 7.87 (dd,J=8.3 Hz,J'=1.8 Hz,1H,Ar); 7.93 (s,1H,Ar); 11.57 (s,1H,exch.D$_2$O,NH); 11.69 (s,1H,exch.D$_2$O,NH); 13.51 (s,1H,exch.D$_2$O,NH).

EXAMPLE 4

2-[2,3-Dihydro-5-(3,6-dihydro-6-methyl-2-oxo-2H-1,3,4-thiadiazin-5-yl)-2-oxo-1H-indol-3-ylidene]-hydrazine carbothioamide.

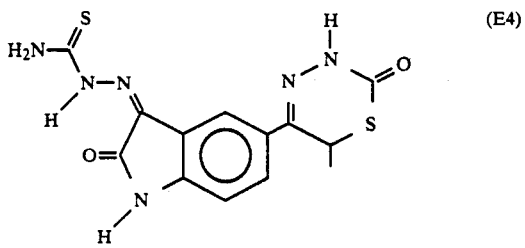

A mixture of 1g (3.6mmol) 1,3-dihydro-5-(3,6-dihydro-6-methyl-2-oxo-2H-1,3,4-thiadiazin-5-yl)-3H-indole-2,3 (1H)-dione, 0.33 g (3.6mmol) thiosemicarbazide in 30 ml ethanol were refluxed for 30 minutes. Filtration of the cooled resulting suspension, yielded the desired compound as yellow crystals.

Yield: 79%.
m.p.: 300° C.
IR (KBr): $\upsilon$ = 3,250; 1,698; 1,648; 1,625; 1,608; 1,590; 1,485; 1,210; 1,140 cm$^{-1}$.
NMR (DMSO-d$_6$): $\delta$ = 1.52 (d,J = 7.1 Hz,3H,CH$_3$—CH); 4.65 (q, J = 7.1 Hz,1H,CHCH$_3$); 7.02 (d,J = 8.3 Hz,1H,Ar); 7.81 (dd, J = 8.3 Hz,J' = 1.7 Hz,1H,Ar); 8.12 (d,J' = 1.4 Hz,1H,Ar); 8.81 (s,1H,exch.-D$_2$O,NH); 9.12 (s,1H,exch.D$_2$O,NH); 11.43 (s,1H, exch.D$_2$O,NH); 11.70 (s,1H,exch.D$_2$O,NH); 12.41 (s,1H, exch.D$_2$O,NH).

EXAMPLE 5

5-(3,6-Dihydro-6-methyl-2-oxo-2H-1,3,4-thiadiazin-5-yl)-1H-indole-2,3-dione 3-phenylhydrazone:

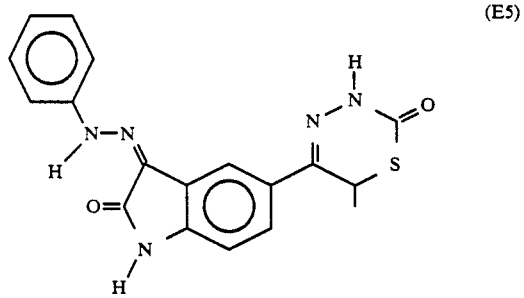

A mixture of 1g (3.6mmol) 1,3-dihydro-5-(3,6-dihydro-6-methyl-2-oxo-2H-1,3,4-thiadiazin-5-yl)-3H-indole-2,3 (1H)-dione, 0.4 g (3.7mmol) phenylhydrazine in 30 ml ethanol was refluxed for 15 minutes. Filtration yielded 950 mg yellow crystals which were purified by column chromatography on silica (eluent : chloroform with 1% methanol).

Yield: 770 mg (58%).
m.p.: 296° C.
IR (KBr): $\upsilon$ = 3,150; 1,692; 1,615; 1,595; 1,560; 1,240; 1,150 cm$^{-1}$.
NMR (DMSO-d$_6$): $\delta$ = 150 ppm (d,J = 7.1 Hz,3H,CH$_3$—CH); 4.83 (q,J = 7.1 Hz,1H,CH$_3$CH); 6.9-8.1 (m,8H,Ar); 11.26 (s,1H,exch. D$_2$O,NH); 11.64 (s,1H,exch.D$_2$O,NH); 12.74(s,1H,exch.D$_2$O, NH—N).

Alternative preparation 400 mg (4.3mmol) aniline in 10 ml water containing 2.5 ml hydrochloric acid were diazotized at 0.5oC with a cold solution of 300 mg (4.3mmol) sodium nitrite in 8 ml water. This solution was added dropwise to a solution of 1.0 g (3.0mmol) 5-(3,6-dihydro-6-methyl-2-oxo-2H-1,3,4-thiadiazin-5-yl)-1,3-dihydro-2H-indol-2-one in 20 ml ethanol and 20 ml DMF. The mixture was stirred 1 hour at room temperature. The precipitate was filtered off, washed with methylene chloride and methanol and dried under vacuum.

m.p.,IR,NMR were identical to those of the product obtained by the previous method.

EXAMPLE 6

1,3-6-Dihydro-5-(3,6-dihydro-6-methyl-2-oxo-2H-1,3,4-thiadiazin-5-yl)-3-phenylimino-2H-indol-2-one

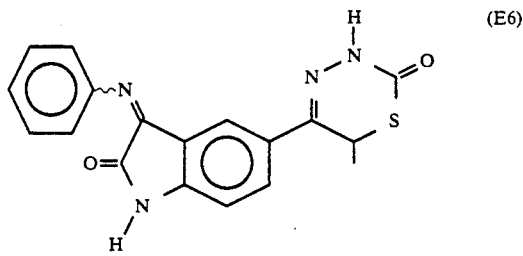

A mixture of 2 g (7.3mmol) 1,3-dihydro-5-(3,6-dihydro-6-methyl-2-oxo-2H-1,3,4-thiadiazin-5-yl)-3H-indole-2,3 (1H)-dione and 0.68 g (7.3mmol) ankiline in 50 ml ethanol was refluxed for 1 hour. After cooling, yellow crystals were filtered off and dried at 40° C under vacuum.

Yield: 78% (as a mixture syn +anti).
m.p.: 290° C.
IR (KBr): $\upsilon$ = 3,200; 1,769; 1,735; 1,645; 1,615; 1,485; 1,305 1,205 cm$^{-1}$.
NMR (DMSO-d$_6$): mixture of syn +anti: $\delta$ = 1.27 ppm (d,J = 7.1 Hz,3×0.72H,CH$^3$—CH); 1.48 (d,J = 7.1 Hz,3×0.28H,CH$_3$CH); 4.07 (q,J = 7.1 Hz,0.72H,CH$_3$CH); 4.80 (q,J = 7.1 Hz,0.28H,CH$_3$CH); 6.7-8.1 (m, 8H,Ar; 11.2 (m,1H,exch.D$_2$O,NH); 11.57 (m,0.72H,exch.D$_2$O,NH); 11.68 (m,0.28H, exch.-D$_2$O,NH).
MS: 18,28,51,77,218,233,234,235,261,262,322,323,350,351,352.Molecular ion : 350.0823 (Theoretical 350.08374 for C$_{18}$H$_{14}$N$_4$O$_2$S).

Alternative method 20 g (76mmoles) 5-(3,6-dihydro-6-methyl-2-oxo-2H-1,3,4-thiadiazin-5-yl)-1,3-dihydro-2H-indol-2-one in 700 ml 1/1 methanol/ethanol were heated to 60° C 9 g (8.3 mmoles) nitrosobenzene were added portionswise, then 4 ml piperidin dropwise. The suspension became clear, then a precipitate appeared after a few minutes. Stirring was continued for 10 minutes, and the suspension cooled. The precipitate was filtered off, washed with methylene chloride and dried under vacuum, yielding 15.5 g (58%) of the desired compound, identical to that obtained by the previous method.

EXAMPLE 7

5-(3,6-Dihydro-6-methyl-2-oxo-2H-1,3,4-thiadiazin-5-yl)-1H-indole-2,3-dione 3-hydrazone

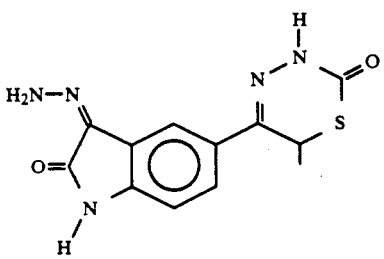

1 g (3.6mmol) 1,3-dihydro-5-(3,6-dihydro-6-methyl-2-oxo-2H -1,3,4-thiadiazin-5-yl)-3H-indole-2,3 (1H)-dione were added to a solution of 10 ml hydrazine hydrate in 10 ml ethanol at room temperature. The color changed from red to yellow. 60 ml water were added. After filtration, 150 mg of yellow crystals were isolated.

Yield: 14%.
m.p.: 268° C.
IR (KBr): $\upsilon$=3,400; 3,200; 1,690; 1,620; 1,600; 1,480; 1,190 cm$^{-1}$.
NMR (DMSO-d$_6$): $\delta$=1.48 ppm (d,J=7.1 Hz,3H,CH$_3$—CH); 4.77 (q,J=7.1 Hz,1H,CH$_3$—CH); 6.95 (d,J=8.3 Hz,1H,Ar); 7.65 (dd, J=8.3 Hz,J'=1.7 Hz,1H,Ar); 7.79 (d,J'=1.7 Hz,1H,Ar); 9.80 (m,1H,exch.D$_2$O,NH); 11.60 (m,1H,exch.D$_2$O,NH).

EXAMPLE 8

1,3-Dihydro-5-(3,6-dihydro-6-methyl-2-oxo-2H-1,3,4-thiadiazin-5-yl)-3-phenylamino-2H-indol-2-one, hydrochloride

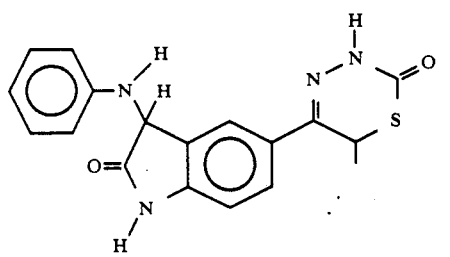

1 g (2.8mmol) 1,3-Dihydro-5-(3,6-dihydro-6-methyl-2-oxo-2H -1,3,4-thiadiazin-5-yl)-3-phenylimino-2H-indol-2-one (E6) and 1.87 g (28mmol) powdered zinc in 20 ml glacial acetic acid were refluxed for 10 minutes. The excess of zinc was removed by filtration and washed with acetic acid. 100 ml water were added to the filtrate and the precipitate was filtered, washed with water until neutral, and dried under vacuum. This compound was kept under argon since it reverts to the starting material in presence of air. The crystals of the free base were suspended in a 1/5 mixture of methanol/ethyl ether (30 ml) and about 5 ml of a saturated solution of HCl gas in ethyl ether were added. After 1 hour of stirring, the white precipitate was filtered off, washed with ether and dried.

Overall yield: 730 mg (66%).
m.p.: 335° C. (hydrochloride); 164° C. dec (free base).
Hydrochloride: IR (KBr):$\upsilon$=3,400; 3,200; 1,735; 1,625; 1,500 cm$^{-1}$.
NMR (DMSO-d$_6$): $\delta$=1.43 ppm (d,J=7.1 Hz,3H,CH$_3$—CH); 3.38 (q, J=7.1 Hz,1H,CH$_3$—CH); 5.17 (s,1H,NHCH); 5.36 (m,exch.D$_2$O,HCl+NH Ar); 6.5-6.6 (m,3H,Ar); 6.9-7.1 (m,3H,Ar); 7.6-7.7 (m,2H,Ar); 10.81 (s,1H,exch.D$_2$O,NH); 11.55 (s,1H,exch.-D$_2$O,NH).

EXAMPLE 9

[5-(3,6-Dihydro-6-methyl-2-oxo-2H-1,3,4-thiadiazin-5-yl)-1,2-dihydro-2-oxo-3H-indol-3-ylidene]-propane-dinitrile

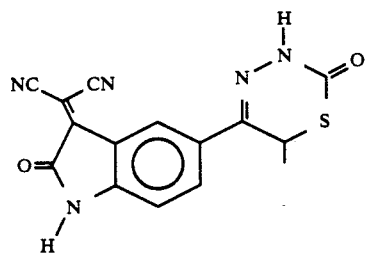

500 mg (1.8mmol) 1,3-dihydro-5-(3,6-dihydro-6-methyl-2-oxo-2H-1,3,4-thiadiazin-5-yl)-3H-indole-2,3 (1H)-dione, 0.73 g (6ep.) malononitrile in 50 ml ethanol were stirred at room temperature for 0.5 hour. The precipitate was filtered and dried under vacuum. Dark violet crystals.

Yield: 73%.
m.p.: 276° C.
IR (KBr): $\upsilon$=3,450; 3,100; 2,240 (weak); 1,745; 1,642; 1,622; 1,600; 1,305; 1,205 cm$^{-1}$.
NMR (DMSO-d$_6$): $\delta$=1.49 ppm (d,3H,J=7.2 Hz, CH$_3$—CH); 4.68 (q,1H,J=7.2 Hz,CH$_3$CH); 7.02 (d,1H,J=8.4 Hz,Ar); 7.94 (dd,J=8.4 Hz,J'=1.2 Hz,1H,Ar); 11.47 (s,1H,exch.D$_2$O,NH); 11.77 (s,1H,exch.D$_2$O,NH).

EXAMPLE 10

1,3-Dihydro-5-(3,6-dihydro-6-methyl-2-oxo-2H-1,3,4-thiadiazin-5-yl)-3-phenylmethylene-2H-indol-2-one

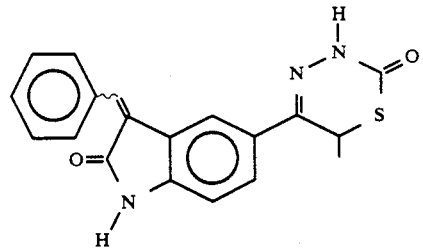

A mixture of 1g (3.8mmol) 5-(3,6-dihydro-6-methyl-2-oxo-2H -1,3,4-thiadiazin-5-yl)-1,3-dihydro-3,3-dimethyl-2H-indol-2-one, 0.4 g (3.8mmol) benzaldehyde and 0.05 g (0.5mmol) piperidine in 5 ml methanol was refluxed with stirring for 45 minutes. After cooling at room temperature a precipitate was collected, washed with methanol and dried to give 1.1 g of yellow crystals.

Yield: 83%.
m.p.: 263° C.
IR (KBr): $\upsilon$=3,300; 1,690; 1,650; 1,615; 1,200 cm$^{-1}$.
NMR (DMSO-d$_6$): mixture of E/Z (about 70/30) $\delta$=1.44 ppm (d,J=7.1 Hz,3×0.7H,CH$_3$CH); 1.53 (d,J=7.1 Hz,3×0.3H,CH$_3$CH); 4.51 (q,J=7.1 Hz,0.7H,CHCH$_3$); 4.77 (q,J=7.1 Hz,0.3H,CHCH$_3$); 6.90-8.45 (m,9H,Ar and Ar—CH=); 10.91

(s,0.3+0.7H,exch. D$_2$O,NH); 11.57 (s,0.7H,exch.-D$_2$O,NH); 11.66 (s,0.3H,exch. D$_2$O,NH).

EXAMPLE 11

1,3,-Dihydro-5-(3,6-dihydro-6-methyl-2-oxo-2H-1,3,4-thiadiazin-5-yl)-3-phenoxyimino-2H-indol-2-one

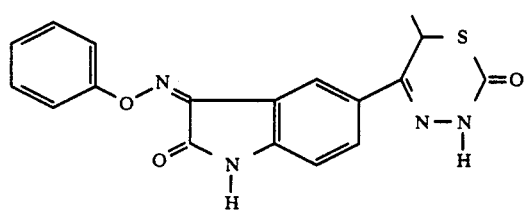
(E11)

Starting from 1,3-dihydro-5-(3,6-dihydro-6-methyl-2-oxo-2H-1,3,4-thiadiazin-5-yl)-3H-indole-2,3(1H)-dione and phenoxylamine, and following the method described in Example 1, the desired compound was obtained.

Yield: 41%.
m.p.: 212° C.
IR (KBr): $\nu$=1,735; 1,615; 1,595; 1,485; 1,300; 1,195 cm$^{-1}$.
NMR (DMSO-d$_6$): $\delta$=1.51 (d,J=7 Hz,3H,CH$_3$CH); 4.79 (q,J=7 Hz,1H,CHCH$_3$); 7.04 (d,J=8 Hz,1H,Ar); 7.2-7.6 (m,5H,Ar phenyl); 7.94 (dd,J=8 Hz,J'=1.7 Hz,Ar); 8.51 (d,J'=1.7 Hz,1H,Ar); 11.2 (m,1H,exch.-D$_2$O,NH); 11.7 (m,1H,exch.D$_2$O,NH).

EXAMPLE 12

5-(3,6-Dihydro-6-methyl-2-oxo-2H-1,3,4-thiadiazin-5-yl)-1H-indole-2,3-dione
3-[2-(aminomethanimino)hydrazone]

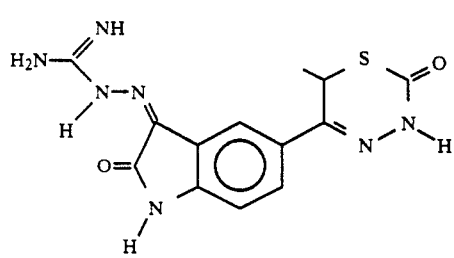
(E12)

Starting from 1,3-dihydro-5-(3,6-dihydro-6-methyl-2-oxo-2H-1,3,4-thiadiazin-5-yl)-3H-indole-2,3(1H)-dione and aminoguanidine bicarbonate and following the method described in Example 1, the desired compound was obtained.

Yield: 47%.
m.p.: 225° C. dec.
IR (KBr): $\nu$=3,300; 1,690; 1,610; 1,470; 1,430 cm$^{-1}$.
NMR (DMSO-d$_6$): $\delta$=1.47 (d,J=7.1 Hz,3H,CH$_3$CH); 4.67 (q, J=7.1 Hz,1H,CH$_3$CH); 6.76 (s,3H,exch.D$_2$O NH,NH$_2$); 6.88 (d,J=8.2 Hz,1H,Ar); 7.68 (dd,J=8.2 Hz,J'=1.8 Hz,1H,Ar); 8.74 (d,J'=1.8 Hz,1H,Ar); 10.48(s,1H,exch.D$_2$O,NH); 11.56 (s,1H,exch.D$_2$O,NH).

EXAMPLE 13

5-(3,6-Dihydro-6-methyl-2-oxo-2H-1,3,4-thiadiazin-5-yl)-1H-indole-2,3-dione
3-[2-(4,5-dihydro-1H-2-imidazolyl)-hydrazone]

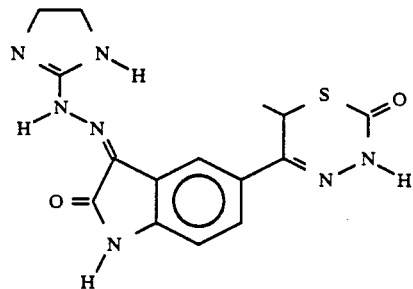
(E13)

Starting from 1,3-dihydro-5-(3,6-dihydro-6-methyl-2-oxo-2H-1,3,4-thiadiazin-5-yl)-3H-indole-2,3-(1H)-dione and 2-hydrazino-2-imidazolin hydrobromide and following the method described in Example 1, the desired compound was obtained.

Yield: 41%.
m.p.: 243° C. dec.
IR (KBr): $\nu$=1,680; 1,610; 1,510; 1,165 cm$^{-1}$.
NMR (DMSO-d$_6$): $\delta$=1.49 (d,J=7.1 Hz,3H,CH$_3$CH); 3.34 (s, 4H,NCH$_2$CH$_2$N); 4.58 (q,J=7.1 Hz,1H,CH$_3$CH); 6.8 (d, J=8.3 Hz,1H,Ar); 7.5-7.7 (m, containing at 7.63,s,2H, exch.D$_2$O,NH,NH; and dd,J=8.3 Hz,J'=1.7 Hz,1H,Ar); 8.72 (d,J'=1.7 Hz,1H,Ar); 10.50 (s,1H,exch.D$_2$O,NH); 11.58 (s,1H,exch.D$_2$O,NH).

EXAMPLE 14

1,3-Dihydro-5-(3,6-dihydro-6-methyl-2-oxo-2H-1,3,4-thiadiazin-5-yl)-3-(4-dimethylaminophenylimino)-2H-indol-2-one

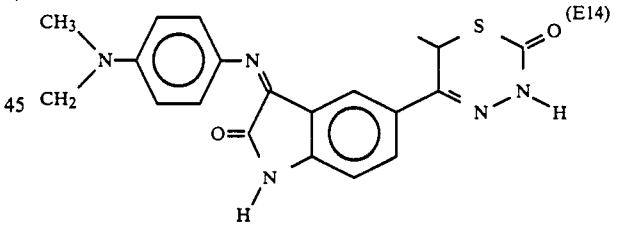
(E14)

Starting from 1,3-dihydro-5-(3,6-dihydro-6-methyl-2-oxo-2H-1,3,4-thiadiazin-5-yl)-3H-indole-2,3(1H)-dione and N,N-dimethyl p-phenylene diamine and following the method described in Example 1, the desired compound was obtained.

Yield: 81%.
m.p.: 261° C.
IR (KBr): $\nu$=3,200; 1,740; 1,610; 1,565 cm$^{-1}$.
NMR (DMSO-d$_6$). Mixture of two isomers in a ratio of about 45/55

A (major isomer): 1.36 (d,J=7.2 Hz,3H,CH$_3$CH); 2.99 (s,6H,CH$_3$NCH$_3$); 4.30 (q,J=7.2 Hz,1H,CH$_3$CH); 6.6-8.0 (m,7H,Ar); 11.10 (m,1H,exch.D$_2$O,NH); 11.65 (m,1H,exch. D$_2$O,NH).

B (minor isomer): 1.48 (d,J=7.1 Hz,3H,CH$_3$CH); 3.02 (s,6H,CH$_3$NCH$_3$); 4.79 (q,J=7.1 Hz,1H,CH$_3$CH); 6.6-8.0 (m,7H,Ar); 11.10 (m,1H,exch.D$_2$O,NH); 11.65 (m,1H,exch. D$_2$O,NH).

EXAMPLE 15

Methyl 2-[2,3-dihydro-5-(3,6-dihydro-6-methyl-2-oxo-2H-1,3,4-thiadiazin-5-yl)-2-oxo-1H-indol-3-ylidene]hydrazine carboxylate

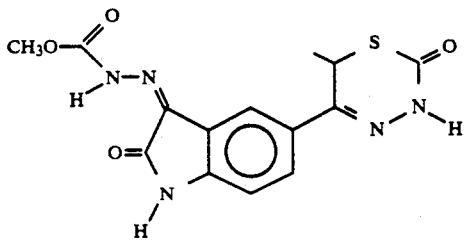
(E15)

Starting from 1,3-dihydro-5-(3,6-dihydro-6-methyl-2-oxo -2H-1,3,4- thiadiazin-5-yl)-3H-indole-2,3(1H)-dione and methylcarbazate and following the method described in Example 1, the desired compound was obtained.

Yield: 33%.
m.p.: 201° C.
IR (KBr): υ=3,200; 1,735; 1,610; 1,525; 1,180 cm$^{-1}$.
NMR (DMSO-d$_6$): δ=1.50 (d,J=7.0 Hz,3H,CH$_3$CH); 3.84 (s,3H, CH$_3$O); 4.81 (q,J=7.0 Hz,1H,CH$_3$CH); 6.97 (d,J=8.3 Hz,1H,Ar); 7.84 (d,J=8.3 Hz,1H,Ar); 8.34 (s,1H, Ar); 11.02 (s,1H,exch.-D$_2$O,NH); 11.25 (s,1H,exch.D$_2$O,NH); 11.70 (s,1H,exch.D$_2$O,NH).

EXAMPLE 16

1,3-Dihydro-5-(3,6-dihydro-6-methyl-2-oxo-2H-1,3,4-thiadiazin-5-yl)-3-(2-nitrophenylmethylene)-2H-indol-2-one

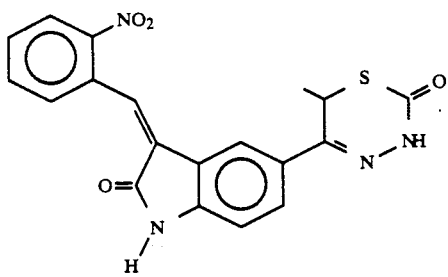
(E16)

Starting from 5-(3,6-dihydro-6-methyl-2-oxo-2H-1,3,4-thiadiazin-5-yl)-1,3-dihydro-2H-indol-2-one and 2 nitro benzaldehyde and following the method described in Example 10, the desired compound was obtained.

Yield: 33%.
m.p.: 258° C.
IR (KBr): υ=3,200; 1,710; 1,645; 1,605; 1,520 cm$^{-1}$.
NMR (DMSO-d$_6$): δ=1.33 (d,J=7.1 Hz,3H,CH$_3$CH); 4.35 (d,J=7.1 Hz,1H,CH$_3$CH); 6.9–8.4 (m,8H including 1H vinyl at 7.33 ppm,3H,Ar and 4Hphenyl ring); 10.97 (s,1H, exch.D$_2$O,NH); 11.53 (s,1H,exch.D$_2$O,NH).

EXAMPLE 17

1,3-Dihydro-5-(3,6-dihydro-6-methyl-2-oxo-2H-1,3,4-thiadiazin-5-yl)-3-[(2-hydroxyphenyl)methylene]-2H-indol-2-one

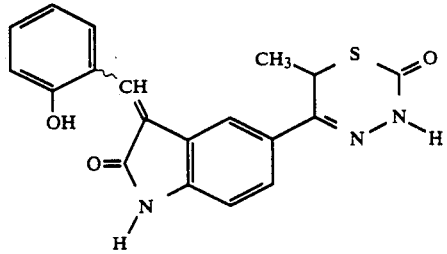
(E17)

Starting from 5-(3,6-dihydro-6-methyl-2-oxo-2H-1,3,4-thiadiazin-5-yl)-1,3-dihydro-2H-indol-2-one and 2-hydroxy benzaldehyde and following the method described in Example 10, the desired compound was obtained.

Yield: 62%.
m.p.: 233° C.
IR (KBr): υ=3,200; 1,680; 1,640; 1,610; 1,455; 1,225 cm$^{-1}$.
NMR (DMSO-d$_6$): δ=1.45 (d,J=7.1 Hz,3H,CH$_3$CH); 4.50 (q,J=7.1 Hz,3H,CH$_3$CH); 6.9–8.1 (m,8H including 4H phenyl, 3H,Ar and 1H,vinyl); 10.26 (m,1H,exch.D$_2$O,OH); 10.82 (s,1H,exch.D$_2$O,NH); 11.55 (s,1H,exch.D$_2$O,NH).

EXAMPLE 18

1,3-Dihydro-5-(3,6-dihydro-6-methyl-2-oxo-2H-1,3,4-thiadiazin-5-yl)-3-(4-pyridylmethylene-2H,indol-2-one

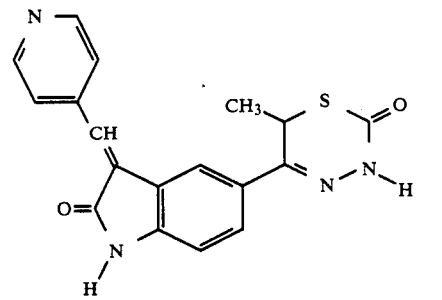
(E18)

Starting from 5-(3,6-dihydro-6-methyl-2-oxo-2H-1,3,4-thiadiazin-5-yl)-1,3-dihydro-2H-indol-2-one and pyridine 4-carboxaldehyde and following the method described in Example 10, the desired compound was obtained.

Yield: 85%.
m.p.: 319° C.
IR (KBr): υ=1,690; 1,600; 1,200 cm$^{-1}$.
NMR (DMSO-d$_6$): δ=mixture of two isomers Z and E in a ratio of about 40/60

1.42 (d,J=6.3 Hz,3H,CH$_3$CH, major isomer); 1.52 (d, J=6.3 Hz,3H,CH$_3$CH, minor isomer); 4.52 (q,J=6.3 Hz,1H,CH$_3$ CH, major isomer); 4.75 (q,J=6.3 Hz,1H,CH$_3$CH, minor isomer); 6.9–8.8 (m,8H including 1H,vinylic, 3H,Ar and 4H,pyridine); 10.98 (s,1H,exch.-D$_2$O,NH); 11.57 and 11.67 (2s,1H,exch.D$_2$O,NH2 isomers).

EXAMPLE 19

1,3-Dihydro-5-(3,6-dihydro-6-methyl-2-oxo-2H-1,3,4-thiadiazin-5-yl)-3-(3-pyridylmethylene)-2H-indol-2-one

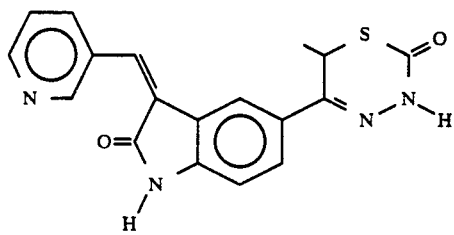

(E19)

Starting from 5-(3,6-dihydro-6-methyl-2-oxo-2H-1,3,4-thiadiazin-5-yl)-1,3-dihydro-2H-indol-2-one and pyridine 3-carboxaldehyde and following the method described in Example 10, the desired compound was obtained.

Yield: 75%.

m.p.: 285° C.

IR (KBr): $\nu = 1,690$; 1,650; 1,615; 1,210 cm$^{-1}$.

NMR (DMSO-d$_6$): mixture E+Z in a ratio of about 1 to 1. 1.43 (d,J=6.7 Hz,3H,CH$_3$CH, isomer A); 1.53 (d,J=6.7 Hz,3H CH$_3$CH,isomer B); 4.52 (q,J=6.7 Hz,1H,CH$_3$CH,isomer A); 4.76 (q,J=6.7 Hz,1H,CH$_3$CH,isomer B); 6.9–9.3 (m,8H including 1H vinyl, 4H pyridine and 3H Ar); 10.96 (s,1H, exch.-D$_2$O,NH); 11.57 and 11.67 (2s,1H,exch.D$_2$O,NH isomer A and B).

EXAMPLE 20

1,3-Dihydro-5-(3,6-dihydro-6-methyl-2-oxo-2H-1,3,4-thiadiazin-5-yl)-3-(2-pyridylmethylene)-2H-indol-2-one

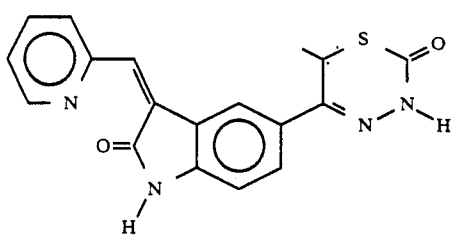

(E20)

Starting from 5-(3,6-dihydro-6-methyl-2-oxo-2H-1,3,4-thiadiazin-5-yl)-1,3-dihydro-2H-indol-2-one and pyridine 2-carboxaldehyde and following the method described in Example 10, the desired compound was obtained.

Yield: 77%.

m.p.: 296° C.

IR (KBr): $\nu = 3,150$; 1,700; 1,635; 1,610 cm$^{-1}$.

NMR (DMSO-d$_6$): $\delta = 1.61$ (d,J=7.1 Hz,3H,CH$_3$CH); 4.69 (q,J=7.1 Hz,1H,CH$_3$CH); 6.96 (d,J=8.3 Hz,1H,Ar); 7.48–8.04 (m,5H including 2H Ar, 1H vinylic and 2H pyridine); 8.9–9.0 (m,1H,pyridine); 9.74 (s,1H,pyridine); 10.91 (s,1H,exch.D$_2$O, NH); 11.64 (s,1H,exch.D$_2$O, NH).

EXAMPLE 21

5-(3,6-Dihydro-6-methyl-2-oxo-2H-1,3,4-thiadiazin-5-yl)-1H-indole-2,3-dione 3-[(4-methyl)phenylhydrazone]

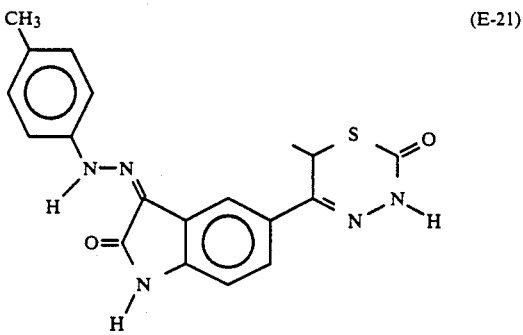

(E-21)

A mixture of 1.5 g (4.3 mmol) 1,3-dihydro-5-(3,6-dihydro-6-methyl-2-oxo-2H-1,3,4-thiadiazin-5-yl)-3-phenylimino-2H-indol-2-one, and 0.75 g (4.5 mmol) 4 methylphenylhydrazine in 20 ml acetonitrile was refluxed 2 hours. The mixture was cooled, filtered off and the residue was washed with hot 1/1 methanol/water. After drying under vacuum orange crystals were obtained.

Yield: 92% m.p.: 285° C.

IR (KBr): $\nu = 1,680$; 1,620; 1,550; 1,240 cm$^{-1}$.

NMR (DMSO-d$_6$): $\delta = 1.50$ (d,J=7.1 Hz,3H,CH$_3$CH); 2.29 (s,3H,CH$_3$Ar); 4.85 (q,J=7.1 Hz,1H,CH$_3$CH); 7.00 (d,J=8.3 Hz,1H,Ar); 7.20 (d,AB,J=8.4 Hz,2H,phenyl); 7.39 (d,AB,J=8.4 Hz,2H,phenyl); 7.73 (dd,J=8.3 Hz,J'=1.8 Hz,1H, Ar); 7.99 (d,J=1.8 Hz,1H,Ar); 11.26 (s,1H,exch.D$_2$O, NH); 11.66 (s,1H,exch.D$_2$O,NH); 12.74 (s,1H,exch.D$_2$O, NH).

EXAMPLE 22

5-(3,6-Dihydro-6-methyl-2-oxo-2H-1,3,4-thiadiazin-5-yl)-1H-indole-2,3-dione 3-[(phenylmethyl)hydrazone]

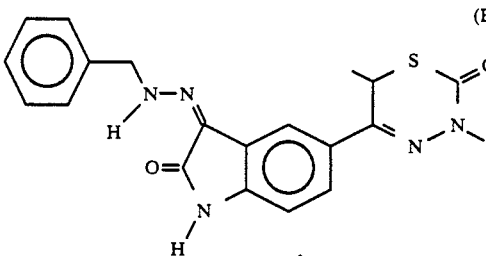

(E22)

Starting from 1,3-dihydro-5-(3,6-dihydro-6-methyl-2-oxo-2H-1,3,4-thiadiazin-5-yl)-3-phenylimino-2H-indol-2-one, and benzylhydrazine dihydrochloride and following the method described in Example 21, the desired compound was obtained.

Yield: 24% m.p.: 202° C.

IR (KBr): $\nu = 3,200$; 1,665; 1,605; 1,550 cm$^{-1}$.

NMR (DMSO-d$_6$): $\delta = 1.46$ (d,J=7.0 Hz,3H,CH$_3$CH); 4.7–4.8 (m,3H,ArCH$_2$+CHCH$_3$); 6.94 (d,J=8.3 Hz,1H,Ar); 7.2–7.4 (m,5H,phenyl ring); 7.64 (d,J=8.3 Hz,1H,Ar); 7.80 (s,1H, Ar); 11.03 (s,1H,exch.-

D$_2$O,NH); 11.37 (s,1H,exch.D$_2$O,NH); 11.61 (s,1H,exch.D$_2$O,NH).

EXAMPLE 23

Ethyl[[[2,3-dihydro-5-(3,6-dihydro-6-methyl-2-oxo-2H-1,3,4-thiadiazin-5-yl)-2-oxo-1H-indol-3-ylidene]amino]oxy]acetate

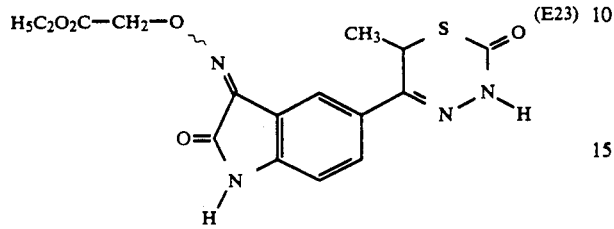

(E23)

Starting from 1,3-dihydro-5-(3,6-dihydro-6-methyl-2-oxo-2H-1,3,4-thiadiazin-5-yl)-3-phenylimino-2H-indol-2-one, and ethyl aminooxyacetate and following the method described in Example 21, the desired compound was obtained.

Yield: 64%
m.p.: 118° C.
IR (KBr): υ=3,200; 1,740; 1,610; 1,210 cm$^{-1}$.
NMR (CDCl$_3$): δ=1.32 (t,J=7.2 Hz,3H,CH$_3$CH$_2$O); 1.67 (d,J=7.2 Hz,3H,CH$_3$CH); 4.1-4.4 (m,q+t,3H,CH$_3$CH$_2$O and CH$_3$CH); 5.07 (s,2H,OCH$_2$CO); 6.97 (d,J=8.4 Hz,1H,Ar); 7.77 (dd,J=8.4 Hz,J'=1.9 Hz,1H,Ar); 8.40 (d,J'=1.9 Hz,1H, Ar); 9.10 (m,2H,exch.D$_2$O,NH,NH).

EXAMPLE 24

5-(3,6-Dihydro-6-methyl-2-oxo-2H-1,3,4-thiadiazin-5-yl) -1H-indole-2,3-dione 3-[4-(1,1-dimethylethyl)phenylhydrazone]

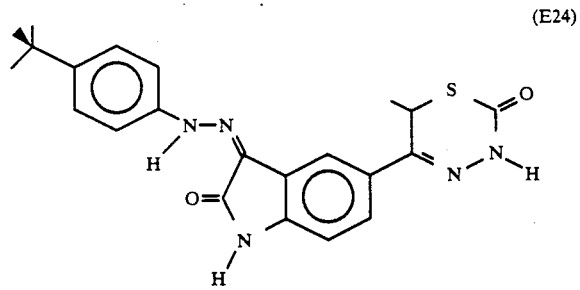

(E24)

Starting from 1,3-dihydro-5-(3,6-dihydro-6-methyl-2-oxo -2H-1,3,4-thiadiazin-5-yl)-3-phenylimino-2H-indol-2-one, and 4t-butyl phenylhydrazine hydrochloride and following the method described in Example 21, the desired compound was obtained.

Yield: 83%
m.p.: 299° C.
IR (KBr): υ=3,200; 1,680; 1,635; 1,615; 1,550; 1,180 cm$^{-1}$.
NMR (DMSO-d$_6$): δ=1.29 (s,9H,t-Bu); 1.50(d,J=7.1 Hz,3H, CH3CH); 4.82 (q,J=7.1 Hz,1H,CH3CH); 7.00 (d,J=8.3 Hz,1H, Ar); 7.41 (s,4H,ArtBu); 7.72 (d,J=8.3 Hz,1H,Ar); 7.99 (s,1H,Ar); 11.26 (s,1H,exch.D$_2$O,NH); 11.66 (s,1H,exch. D$_2$O,NH); 12.77 (s,1H,exch.-D$_2$O,NH).

EXAMPLE 25

5-(3,6-Dihydro-6-methyl-2-oxo-2H-1,3,4-thiadiazin-5-yl) -1H-indole-2,3-dione 3-(cyclohexylhydrazone)

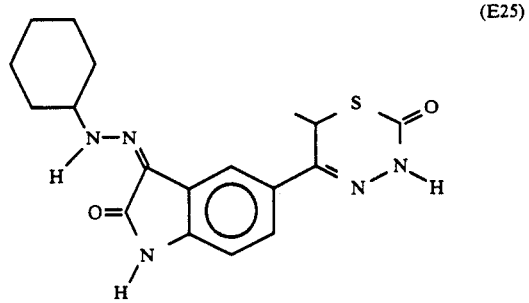

(E25)

Starting from 1,3-dihydro-5-(3,6-dihydro-6-methyl-2-oxo -2H-1,3,4-thiadiazin-5-yl)-3-phenylimino-2H-indol-2-one, and cyclohexylhydrazine and following the method described in Example 21, the desired compound was obtained.

Yield: 54%
m.p.: 217° C.
IR (KBr): υ=3,150; 1,675; 1,635; 1,545; 1,190 cm$^{-1}$.
NMR (DMSO-d$_6$): δ=1.0-2.1 (m,13H,including cyclohexyl ring and d, at 1.47 ppm, J=7.1 Hz,3H,CH$_3$CH); 3.5-3.7 (m, 1H,CHNH); 4.78 (q,J=7.1 Hz,1H,CH$_3$CH); 6.95 (d,J=8.2 Hz, 1H,Ar); 7.64 (dd,J=8.2 Hz,J'=1.6 Hz,1H,Ar); 7.80 (d, J'=1.6 Hz,1H,Ar); 11.03 (s,1H,exch.D$_2$O,NH); 11.16 (d, J=5.3 Hz,1H,exch.D$_2$O,NH); 11.61 (s,1H,exch.D$_2$O,NH).

EXAMPLE 26

5-(3,6-Dihydro-6-methyl-2-oxo-2H-1,3,4-thiadiazin-5-yl)-1H-indole-2,3-dione 3-methylphenylhydrazone)

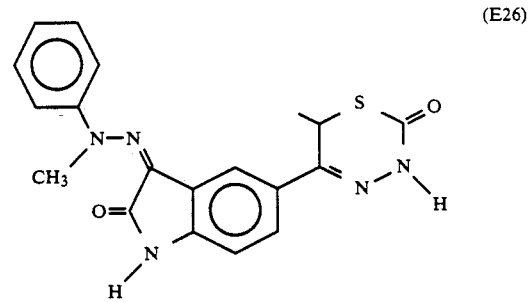

(E26)

Starting from 1,3-dihydro-5-(3,6-dihydro-6-methyl-2-oxo -2H-1,3,4-thiadiazin-5-yl)-3-phenylimino-2H-indol-2-one, and 1-methyl 1-phenylhydrazine and following the method described in Example 21, the desired compound was obtained.

Yield: 47%
m.p.: 260° C.
IR (KBr): υ=1,690; 1,605; 1,540; 1,490 cm$^{-1}$.
NMR (DMSO-d$_6$): δ=1.49 (d,J=7.1 Hz,3H,CH$_3$CH); 3.91 (s,3H,NCH$_3$); 4.83 (q,J=7.1 Hz,1H,CH$_3$CH); 6.9-8.0 (m,8H,including 5H.phenyl ring and 3H,Ar); 11.1 (m,1H,exch.D$_2$O,NH); 11.6 (m,1H,exch.D$_2$O,NH).

EXAMPLE 27

5-(3,6-Dihydro-6-methyl-2-oxo-2H-1,3,4-thiadiazin-5-yl) -1H-indole-2,3-dione 3-(3,4-dichloroohenyl)hydrazone

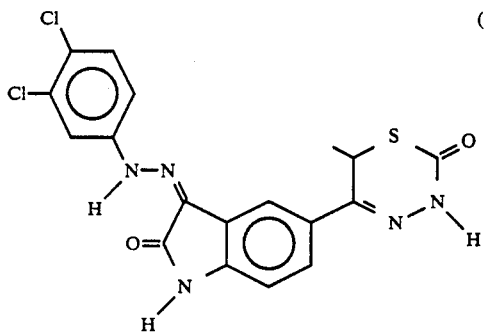
(E27)

Starting from 3-dihydro-5-(3,6-dihydro-6-methyl-2-oxo -2H-1,3,4-thiadiazin-5-yl)-3-phenylimino-2H-indol-2-one, and 3,4-dichlorophenyl hydrazine and following the method described in Example 21, the desired compound was obtained.

Yield: 53% m p.: 295° C.

IR (KBr): $\nu=1,675$; 1,625; 1,560; 1,475 cm$^{-1}$.

NMR (DMSO-d$_6$): $\delta=1.49$ (d,J=7.1 Hz,3H,CH$_3$CH); 4.84 (q,J=7.1 Hz,1H,CH$_3$CH); 7.00 (d,J=8.3 Hz,1H,Ar); 7.4–7.8 (m,4H,3H phenyl ring +1H Ar); 8.02 (s,1H,Ar); 11.32 (s,1H,exch.D$_2$O,NH); 11.67 (s,1H,exch.D$_2$O,NH);12.63 (s, 1H,exch.D$_2$O,NH).

EXAMPLE 28

5-(3,6-Dihydro-6-methyl-2-oxo-2H-1,3,4-thiadiazin-5-yl) -1H-indole-2,3-dione 3-[(4-methoxy)phenylhydrazone]

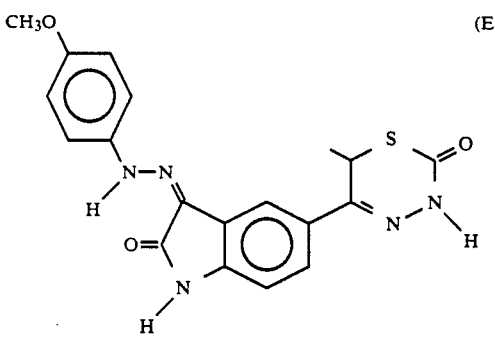
(E28)

Starting from 1,3-dihydro-5-(3,6-dihydro-6-methyl-2-oxo -2H-1,3,4-thiadiazin-5-yl)-3-phenylimino-2H-indol-2-one, and 4-methoxyphenyl hydrazine and following the method described in Example 21, the desired compound was obtained.

Yield: 90% m.p.: 273° C.

IR (KBr): $\nu=3,200$; 1,680; 1,645; 1,620; 1.560 cm$^{-1}$.

NMR (DMSO-d$_6$): $\delta=1.50$ (d,J=7.0 Hz,3H,(CH$_3$CH); 3.76 (s,3H,CH$_3$O); 4.83 (q,J=7.0 Hz,1H,CH$_3$CH); 6.9–7.1 (m,3H 2H phenyl +1H Ar); 7.43 (d,AB,J=9.0 Hz,2H,phenyl); 7.71 (dd,J=8.3 Hz,J'=1.7 Hz,1H,Ar); 7.98 (d,J'=1.7 Hz,1H,Ar); 11.22 (s,1H,exch.D$_2$O,NH); 11.65 (s,1H,exch.D$_2$O,NH); 12.77 (s,1H,exch.D$_2$O,NH).

EXAMPLE 29

5-(3,6-Dihydro-6-methyl-2-oxo-2H-1,3,4-thiadiazin-5-yl) -1H-indole-2,3-dione 3-[(4-chloro)phenylhydrazone]

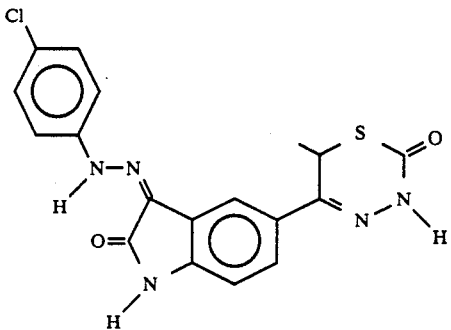
(E29)

Starting from 1,3-dihydro-5-(3,6-dihydro-6-methyl-2-oxo -2H-1,3,4-thiadiazin-5-yl)-3-phenylimino-2H-indol-2-one, and 4-chlorophenyl hydrazine and following the method described in Example 21, the desired compound was obtained.

Yield: 70% m.p.: 283° C.

IR (KBr): $\nu=1,690$; 1,620; 1,560 cm$^{-1}$.

NMR (DMSO-d$_6$): $\delta=1.50$ (d,J=7.0 Hz,3H,CH$_3$CH); 4.84 (q,J=7.0 Hz,1H,CH$_3$CH); 7.01 (d,J=8.3 Hz,1H,Ar); 7.4–7.6 (m,4H,phenyl); 7.75 (dd,J=8.3 Hz,J=1.2 Hz,1H,Ar); 8.00 (d,J'8.2 Hz,1H,Ar); 11.30 (s,1H,exch.D$_2$O,NH); 11.67 (s,1H,exch.D$_2$O,NH);12.69 (s,1H,exch.D$_2$O,NH).

EXAMPLE 30

5-(3,6-Dihydro-6-methyl-2-oxo-2H-1,3,4-thiadiazin-5-yl) -1H-indole-2,3-dione 3-(4-fluoro)phenylhydrazone]

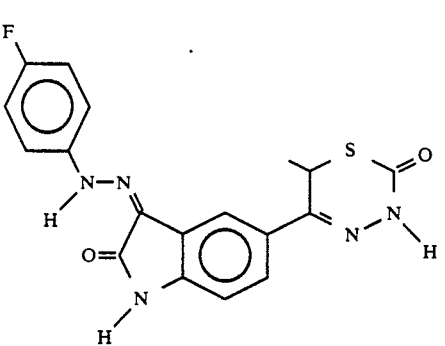
(E30)

Starting from 1,3-dihydro-5-(3,6-dihydro-6-methyl-2-oxo -2H-1,3,4-thiadiazin-5-yl)-3-phenylimino-2H-indol-2-one, and 4-fluorophenyl hydrazine and following the method described in Example 21, the desired compound was obtained.

Yield: 64% m.p.: 291° C.

IR (KBr): $\nu=3,200$; 1,695; 1,620; 1,565, 1,520; 1,150 cm$^{-1}$.

NMR (DMSO-d$_6$): $\delta=1.50$ (d,J=7.0 Hz,3H,CH$_3$CH); 4.84 (q, J=7.0 Hz,1H,CH$_3$CH); 7.01 (d,J=8.3 Hz,1H,Ar); 7.24–7.29(m, 2H,phenyl); 7.50–7.60 (m,2H,phenyl); 7.74 (d,J=8.3 Hz, 1H,Ar); 8.00 (s,1H,Ar); 11.28 (s,1H,exch.D$_2$O,NH); 11.67 (s,1H,exch.D$_2$O,NH); 12.70 (s,1H,exch.D$_2$O,NH).

EXAMPLE 31

5-(3,6-Dihydro-6-methyl-2-oxo-2H-1,3,4-thiadiazin-5-yl) -1H-indole-2,3-dione 3-[(2-trifluoromethyl) phenylhydrazone]

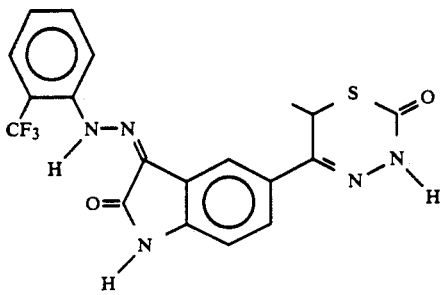
(E31)

Starting from 1,3-dihydro-5-(3,6-dihydro-6-methyl-2-oxo -2H-1,3,4-thiadiazin-5-yl)-3-phenylimino-2H-indol-2-one, and 2-trifluoromethyl phenyl hydrazine and following the method described in Example 21, the desired compound was obtained.

Yield: 44%
m.p.: 304° C.
IR (KBr): υ=3,200; 1,700; 1,610; 1,470, 1,160; 1,115 cm$^{-1}$.
NMR (DMSO-d$_6$): δ=1.51 (d,J=7.1 Hz,3H,CH$_3$CH); 4.83 (q, J=7.1 Hz,1H,CH$_3$CH); 7.0–8.1 (m,7H,including 4H phenyl ring and 3H Ar); 11.42 (s,1H,exch.D$_2$O,NH); 11.68 (s,1H,exch.D$_2$O,NH); 13.28 (s,1H,exch.D$_2$O,NH).

EXAMPLE 32

5-(3,6-Dihydro-6-methyl-2-oxo-2H-1,3,4-thiadiazin-5-yl) -1H-indole-2,3-dione 3-(pentafluorophenylhydrazone)

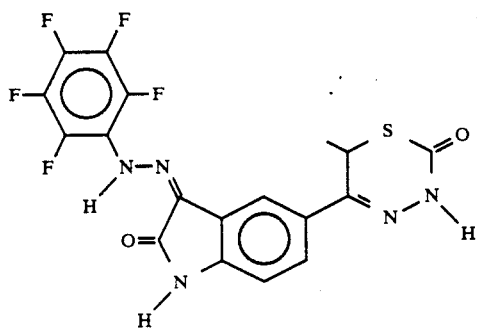
(E32)

Starting from 1,3-dihydro-5-(3,6-dihydro-6-methyl-2-oxo -2H-1,3,4-thiadiazin-5-yl)-3-phenylimino-2H-indol-2-one, and pentafluorophenyl hydrazine and following the method described in Example 21, the desired compound was obtained.

Yield: 92%
m.p.: 285° C.
IR (KBr): υ=3,250; 1,700; 1,620; 1,600, 1,545; 1,525 cm$^{-1}$.
NMR (DMSO-d$_6$): δ=1.47 (d,J=7.1 Hz,3H,(CH$_3$CH); 4.78 (q, J=7.1 Hz,1H,CH$_3$CH); 7.02 (d,J=8.3 Hz,1H,Ar); 7.77 (d,J=8.3 Hz,1H,Ar); 7.88 (s,1H,Ar); 11.47 (s,1H,exch.D$_2$O,NH); 11.65 (s,1H,exch.D$_2$O,NH); 12.51 (s,1H,exch.D$_2$O,NH).

EXAMPLE 33

5-(3,6-Dihydro-6-methyl-2-oxo-2H-1,3,4-thiadiazin-5-yl) -1H-indole-2,3-dione 3-[4-(methylsulfonyl)phenyl hydrazone] monoacetonitrile complex

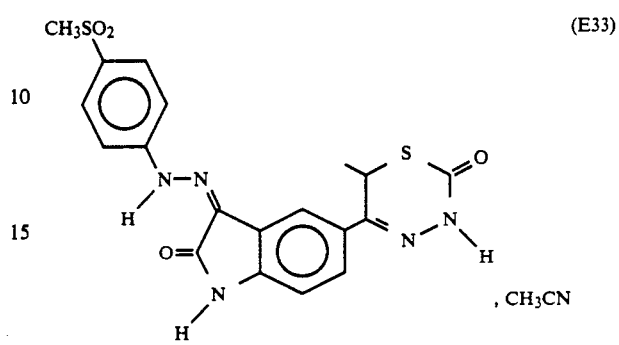
(E33)

Starting from 1,3-dihydro-5-(3,6-dihydro-6-methyl-2-oxo -2H-1,3,4-thiadiazin-5-yl)-3-phenylimino-2H-indol-2-one, and 4 methylsulfonylphenylhydrazine and following the method described in Example 21, the desired compound was obtained.

Yield: 90%
m.p.: 232° C.
This desired compound was crystallised as a complex with 1 equivalent of acetonitrile.
IR (KBr): υ=3,250; 2,250 (CH$_3$CN); 1,690, 1,620; 1,600; 1,560; 1,140 cm$^{-1}$.
NMR (DMSO-d$_6$) δ=1.50 (d,J=7.1 Hz,1H,CH$_3$CH); 2.08 (s,3H,CH$_3$CN); 3.21 (s,3H,CH$_3$SO$_2$); 4.83 (q,J=7.1 Hz,CH$_3$CH); 7.02 (d,J=8.3 Hz,1H,Ar); 7.69 (d,J=8.8 Hz,2H,phenyl); 7.78 (dd,J=8.3 Hz,J'=1.6 Hz,1H,Ar); 7.90 (d,J=8.8 Hz,2H, - phenyl); 8.05 (d,J'=1.6 Hz,1H,Ar); 11.38 (s,1H,exch.D$_2$O, NH); 11.70 (s,1H,exch.D$_2$O,NH); 12.81 (s,1H,exch.D$_2$O,NH).

EXAMPLE 34

4-2-[5-(3,6-Dihydro-6-methyl-2-oxo-2H-1,3,4-thiadiazin -5-yl)2,3-dihydro-2-oxo-1H-indol-3-ylidene1hydrazinol-benzoic acid

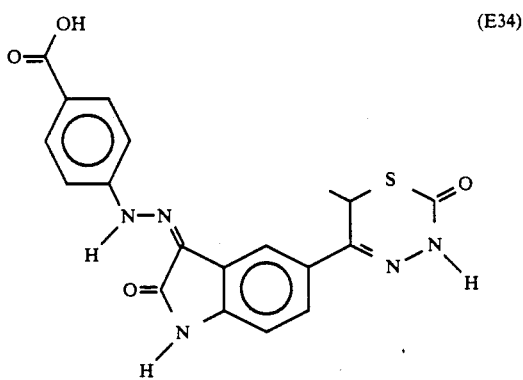
(E34)

Starting from 1,3-dihydro-5-(3,6-dihydro-6-methyl-2-oxo -2H-1,3,4-thiadiazin-5-yl)-3-phenylimino-2H-indol-2-one, and 4 hydrazinobenzoic acid and following the method described in Example 21, the desired compound was obtained.

Yield: 95%
m.p.: >320° C.

IR (KBr): ν=3,200; 1,690; 1,610, 1,570; 1,260; 1,160; cm⁻¹.

NMR (DMSO-d₆): δ=1.50 (d,J=7.1 Hz,1H,CH₃CH); 4.85 (q, J=7.1 Hz,1H,CH₃C$\underline{H}$); 7.02 (d,J=8.3 Hz,1H,Ar); 7.56 (d,AB, J=8.7 Hz,2H,phenyl); 7.77 (dd,J=8.3 Hz,J'=1.7 Hz,1H,Ar); 7.95 (d,AB,J=8.7 Hz,2H,phenyl); 8.03 (d,J'=1.7 Hz,1H,Ar); 11.35 (s,1H,exch.D₂O,N$\underline{H}$); 11.67 (s,1H,exch.D₂O,N$\underline{H}$); 12–13 (m,1H,exch.D₂O,$\overline{\text{COO}}$$\underline{H}$); 12.80 (s,1H,exch.D₂O,N$\underline{H}$).

EXAMPLE 35

5-(3,6-Dihydro-6-methyl-2-oxo-2H-1,3,4-thiadiazin -5-yl)-1H-indole-2,3-dione 3-(2-pyridylhydrazone) monohydrochloride

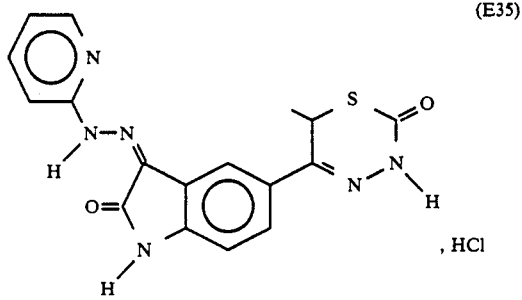

(E35)

Starting from 1,3-dihydro-5-(3,6-dihydro-6-methyl-2-oxo -2H-1,3,4-thiadiazin-5-yl)-3-phenylimino-2H-indol-2-one, and 2-pyridylhydrazine and following the method described in Example 21, the desired compound was obtained.

Yield: 31%
m.p.: 288° C.
IR (KBr): ν=1,680; 1,630; 1,530 cm⁻¹.
NMR (DMSO-d₆): δ=1.49 (d,J=6.9 Hz,3H,CH₃CH); 4.84 (q, J=6.9 Hz,1H,CH₃C$\underline{H}$); 7.08 (d,J=8.2 Hz,1H,Ar); 7.77–8.00 (m,3H,pyridine); 8.42 (d,J=8.0 Hz,1H,Ar); 8.93 (m,1H,-pyridine); 9.15 (s,1H,Ar); 11.71 (s,2H,exch.D₂O,N$\underline{H}$); 13.79 (s,1H,exch.D₂O,N$\underline{H}$).

EXAMPLE 36

5-(3,6-Dihydro-6-methyl-2-oxo-2H-1,3,4-thiadiazin-5-yl) -1H-indole-2,3-dione 3-(3-pyridylhydrazone)

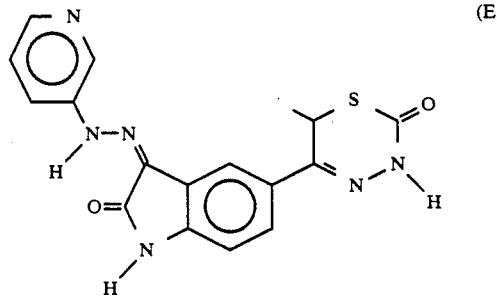

(E36)

Starting from 1,3-dihydro-5-(3,6-dihydro-6-methyl-2-oxo -2H-1,3,4-thiadiazin-5-yl)-3-phenylimino-2H-indol-2-one, and 3-pyridylhydrazine and following the method described in Example 21, the desired compound was obtained.

Yield: 64%
m.p.: 275° C.
IR (KBr): ν=1,700; 1,620; 1,600; 1,570 cm⁻¹.

NMR (DMSO-d₆): δ=1.50 (d,J=7.1 Hz,3H,CH₃CH); 4.84 (q, J=7.1 Hz,1H,CH₃C$\underline{H}$); 7.01 (d,J=8.3 Hz,1H,Ar); 7.37–7.44 (m,1H,Py); 7.77 (d,J=8.3 Hz,1H,Ar); 7.90–7.95 (m,1H,Py); 8.03 (s,1H,Ar); 8.27 (m,1H,Py); 8.79 (m,1H,Py); 11.31 (s,1H,exch.D₂O,N$\underline{H}$); 11.68 (s,1H,exch.D₂O,N$\underline{H}$); 12.63 (s, 1H,exch.D₂O,N$\underline{H}$).

EXAMPLE 37

2-Pyridinecarboxylic acid, 2-[2,3-dihydro-5-(3,6-dihydro-6-methyl-2-oxo-2H-1,3,4-thiadiazin-5-yl)-2-oxo -1H-indol-3-ylidene]hydrazide

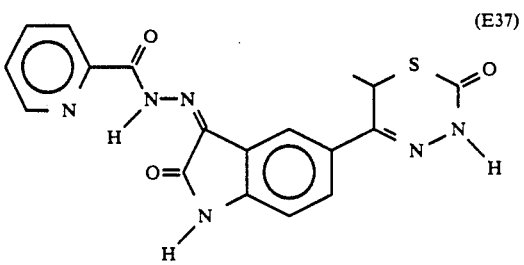

(E37)

Starting from 1,3-dihydro-5-(3,6-dihydro-6-methyl-2-oxo -2H-1,3,4-thiadiazin-5-yl)-3-phenylimino-2H-indol-2-one, and picolyl hydrazide and following the method described in Example 21, the desired compound was obtained.

Yield: 26%
m.p.: >300° C.
IR (KBr): ν=1,740; 1,620; 1,500 cm⁻¹.
NMR (DMSO-d₆): δ=1.58 (d,J=7.1 Hz,3H,CH₃CH); 4.77 (q, J=7.1 Hz,1H,CH₃C$\underline{H}$); 7.04 (d,J=8.3 Hz,1H,Ar); 7.7–7.9 (m, 2H,Ar,pyridine); 8.1–8.3 (m,2H,Ar,pyridine); 8.50 (s, 1H,Ar); 8.92–8.95 (m,1H,Ar); 11.17 (s,1H,exch.D₂O,N$\underline{H}$); 11.88 (s,1H,exch.D₂O,N$\underline{H}$); 12.31(s,1H,exch.D₂O,N$\underline{H}$).

EXAMPLE 38

3-Pyridinecarboxylic acid, 2-[2,3-dihydro-5-(3,6-dihydro-6-methyl-2-oxo-2H-1,3,4-thiadiazin-5-yl)-2-oxo -1H-indol-3-ylidene]hydrazide hydrochloride

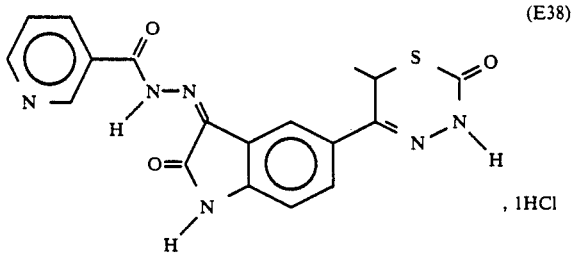

(E38)

Starting from 1,3-dihydro-5-(3,6-dihydro-6-methyl-2-oxo -2H-1,3,4-thiadiazin-5-yl)-3-phenylimino-2H-indol-2-one, and nicotinic acid hydrazide and following the method described in Example 21, the desired compound was obtained.

Yield: 36%
m.p.: >300° C.
IR (KBr): ν=1,700; 1,640; 1,620; 1,665; 1,505; 1,440 cm⁻¹.

NMR (DMSO-d₆): δ=1.51 (d,J=5.7 Hz,3H,CH₃CH); 4.81 (q, J=7 Hz,1H,CH₃C$\underline{H}$); 6.9–8.4 (m,7H,Ar +pyridine); 11.34 (m,1H,exch.D₂O,N$\underline{H}$);

11.67 (m,1H,exch.D₂O,NH); 12.76 (m,1H,exch.-D₂O,NH).

EXAMPLE 39

4-Pyridinecarboxylic acid, 2-[2,3-dihydro-5-(3,6-dihydro-6-methyl-2-oxo-2H-1,3,4-thiadiazin-5-yl)-2-oxo -1H-indol-3-ylidene1hydrazide

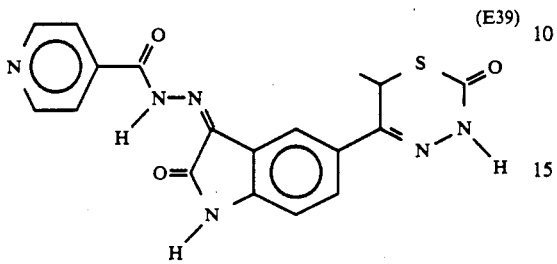

(E39)

Starting from 1,3-dihydro-5-(3,6-dihydro-6-methyl-2-oxo -2H-1,3,4-thiadiazin-5-yl)-3-phenylimino-2H-indol-2-one, and isonicotinic acid hydrazide and following the method described in Example 21, the desired compound was obtained.

Yield: 68%
m.p.: 307° C.
IR (KBr): υ=1,700; 1,610; 1,280 cm-1.
NMR (DMSO-d₆): δ=1.49 (d,J=7.0 Hz,3H,CH₃CH); 4.87 (q, J=7 Hz,1H,CH₃CH); 7.06 (d,J=8.4 Hz,1H,Ar); 7.80 (d,J=5.8 Hz,2H,pyridine); 7.91 (d,J=8.4 Hz,1H,Ar); 8.00 (s,1H,Ar); 8.88 (d,J=5.8 Hz,2H,pyridine); 11.72 (s,1H,exch.D₂O,NH); 12–15 (m,2H,exch.D₂O,2×NH).

EXAMPLE 40

1,3-Dihydro-5-(3,6 dihydro-3,6-dimethyl-2-oxo-2H-1,3,4-thiadiazin-5-yl)-3-phenylimino-2H-indol-2-one

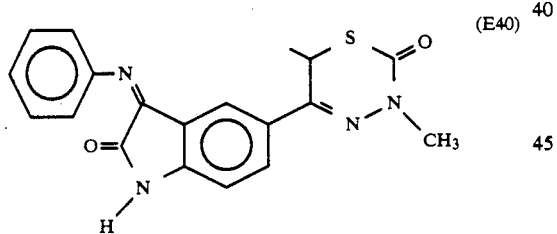

(E40)

4 g (11.4 mmoles)1,3-dihydro-5-(3,6-dihydro-6-methyl-2-oxo-2H-1,3,4-thiadiazin-5-yl)-3-phenylimino-2H-indol-2-one, were dissolved in 35 ml DMF dried over molecular sieves.

1 g (23 mmoles) 60% sodium hydride were added portionwise, then 1.62 g (11.4 mmoles) methyl iodide were added dropwise. The mixture was stirred overnight at room temperature. 100 ml water were added and the solution was extracted with ethyl acetate. The organic phase was washed with water, dried over magnesium sulfate and purified by column chromatography (silica, eluent:methanol 1% in chloroform).

Yield: 29%
m.p.: 253° C.
IR (KBr): υ=3,200; 1,745; 1,615; 1,300 cm⁻¹·
NMR (DMSO-d₆) δ=1.29 (d,J=7.0 Hz,3H,CH₃CH); 3.28 (s, 3H,NCH₃); 4.32 (q,J=7.0 Hz,1H,CH₃CH); 6.9-8.1(m,8H including 5H phenylring and 3H Ar); 11.20(m,1H,exch.D₂O, NH)

A minor isomer (25%) gives supplementary peaks at 1.49 ppm (d,J=7.0 Hz,CH₃CH); 3.45 (s,NCH₃); and 4.85 (q,J=7.0 Hz,CH₃CH).

EXAMPLE 41

5-(3,6-Dihydro-3,6-dimethyl]-2-Oxo-2H-1,3,4-thiadiazin-5-yl)-1H-indole-2,3-dione 3-(phenylhydrazone)

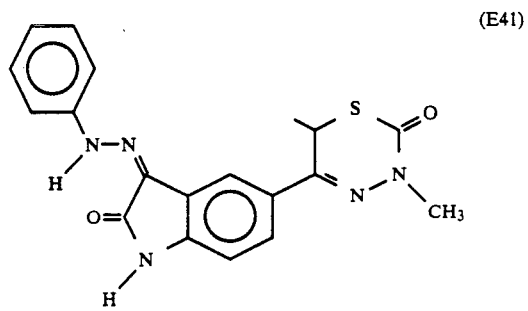

(E41)

Starting from 1,3-dihydro-5-(3,6-dihydro-3,6-dimethyl -2-oxo2H-1,3,4-thiadiazin-5-yl)-3-phenylimino-2H-indol -2-one, and phenyl hydrazine and following the method described in Example 21, the desired compound was obtained.

Yield: 83%
m.p.: 268° C.
IR (KBr): υ=3,150; 1,690; 1,615; 1,555; 1,240; 1,160 cm⁻¹.
NMR (DMSO-d₆) δ=1.51 (d,J=7.0 Hz,3H,CH₃CH); 3.47 (s,3H,NCH₃); 4.85 (q,J=7.0 Hz,1H,CH₃CH); 7.0-8.1 (m,8H including 5H,phenylring and 3H,Ar); 11.31 (s,1H,exch.D₂O,NH); 12.76 (s,1H,exch.D₂O,NH).

EXAMPLE 42

5-(3,6-Dihydro-6-methyl-2-oxo-2H-1,3,4-thiadiazin-5-yl) -1H-indole-2,3-dione 3-[4-trifluoromethylphenylhydrazone]

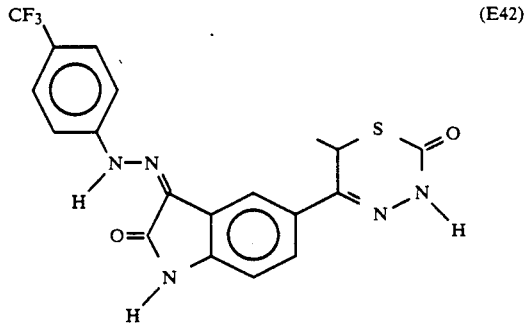

(E42)

1 g (6.2 mmoles) 4-aminobenzotrifluoride, in 16 ml water containing 7 ml hydrochloric acid were diazotized at 0–5° C. with a cold solution of 430 mg (6.3 mmoles) sodium nitrite in 8 ml water. This solution was added dropwise to a solution of 1.62 g (6.2 mmoles)5-(3,6-dihydro-6-methyl-2-oxo-2H-1,3,4-thiadiazin-5-yl)-1,3-dihydro-2H -indol-2-one in 20 ml ethanol and 25 ml DMF. After 1 hour stirring at 0–5° C., the precipitate was filtered off, washed with methylene chloride, and hot methanol and dried under vacuum.

Yield: 51%
m.p.: >300° C.
IR (KBr): υ=1,705; 1,615; 1,570; 1,330 cm⁻¹·
NMR (DMSO-d₆): mixture Z +E : δ=1.52 (2d,3H,CH₃CH); 4.83 (m,1H,CH₃CH); 6.9-8.5 (m,7H including 4H phenylring and 3H Ar); 10.9–12.8 (m,3H,exch.D₂O,NH).

EXAMPLE 43

2-Thiophenecarboxylic acid, 2-[2,3-dihydro-5-(3,6-dihydro-6-methyl-2-oxo-2H-1,3,4-thiadiazin-5-yl)-2-oxo-1H-indol-3-ylidene]hydrazide

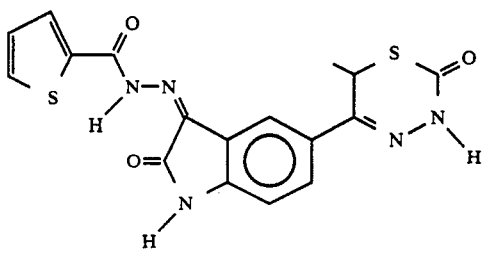

Starting from 1,3-dihydro-5-(3,6-dihydro-6-methyl-2-oxo-2H-1,3,4-thiadiazin-5-yl)-3-phenylimino-2H-indol-2-one and 2-thiophene carboxylic acid hydrazide and following the method described in Example 21, the desired compound was obtained.

Yield; 35%
m.p.; >300° C.
IR: (KBr): υ=3.400, 1.650, 1.615, 1.280, 1 170, 1.110 cm⁻¹.
NMR: (DMSO-d₆) δ=1.50 (d, J=7.1 Hz, 0.9H, CH₃CH, isomer A); 1.60 (d, J=7.0 Hz, 2.1H, CH₃CH, isomer B); 4.6–4.8 (m, 1H, CH₃ CH, isomers A+B); 6.9–8.1 (m, 6H, thiophene H+Ar H); 8.7 (s, 1H, exch. D₂O, NH); 10.4–11.5 (m, 1H, exch. D₂O, NH); 11.7 (m, 1H, exch. D₂O, NH).

EXAMPLE 44

1,3-Dihydro-5-(3,6-dihydro-6-methyl-2-oxo-2H-1,3,4-thiadiazin-5-yl)-3-(2-thienylmethylene)-2H-indole-2-one

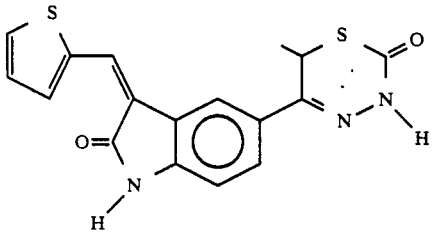

Starting from 5-(3,6-dihydro-6-methyl-2-oxo-2H-1,3,4-thiadiazin-5-yl)-1,3-dihydro-2H-indol-2-one and 2-thiophene carboxaldehyde and following the method described in Example 10, the desired compound was obtained.

Yield: 19%
m.p.: 287° C.
IR: (KBr): υ=3.400, 1.695, 1.652, 1.625, 1.605, 1.200 cm⁻¹.
NMR: (DMSO-d₆) δ=1.46 (d, J=6.4 Hz, 0.5H, CH₃ CH, isomer A); 1.54 (d, J=7.0 Hz, 2.5H, CH₃ CH isomer B); 4.6–4.8 (m, 1H, CH₃ CH, isomers A+B); 6.9–8.3 (m, 7H, 3 indol H, 3 thiophene H and 1 vinyl H); 10.62 (m, 0.15H exch. D₂O, NH, isomer A); 10.88 (m, 0.85H, exch. D₂O, NH, isomer B); 11.59 (m, 0.15H, exch. D₂O, NH, isomer A); 11.65 (m, 0.85H, exch. D₂, NH, isomer B).

EXAMPLE 45

1.3-Dihydro-5-(3 6-dihydro-6-methyl-2-oxo-2H-1,3 4-thiadiazin-5-yl)-3-(3-thienylmethylene-2H-indol-2-one

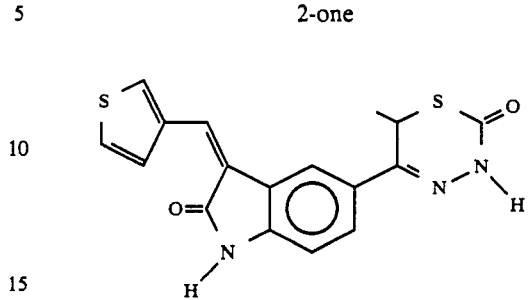

Starting from 5-(3,6-dihydro-6-methyl-2-oxo-2H-1,3,4-thiadiazin-5-yl)-1,3-dihydro-2H-indol-2-one and 3-thiophene carboxaldehyde and following the method described in Example 10, the desired compound was obtained.

Yield: 53%
m.p.: >300° C.
IR: (KBr): υ=3.500, 1.690, 1.650, 1.630, 1.612, 1.210 cm⁻¹.
NMR: (DMSO-d₆) δ=1.53 (d, J=7.1 Hz, 3H, CH₃ CH); 4.7–4.8 (m, 1H, CH₃CH); 6.8–8.9 (m, 7H, 3 thiophene H, 1 vinyl H, 3Ar H); 10.88 (s, 1H, exch. D₂O, NH); 11.63 (s, 1H, exch. D₂O, NH).

Pharmacological Data

1. Measurement of myofibrillar Ca++-dependent Mq++-ATPase activity

The effect on myofibrillar Ca++sensitivity and on maximal activity of myofibrillar Ca++-dependent Mg++-ATPase was determined on canine cardiac myofibrils.

(a) Contractile protein preparation

Cardiac myofibrils free of membrane contaminants were prepared from left ventricular tissue of dog hearts using a modification of the method described by SOLARO et al, Biochem. Biophys. Acta, 245, 259–262, (1971). Before centrifugation, the heart homogenate was filtered through gauze.

After Triton X-100 treatments, the myofibrillar fraction was washed once by resuspension and centrifugation in 10 volumes of 1 mM EGTA, 60 ml KCl, 30 mM imidazole, 2 mM MgCl₂, pH 7.0. The pellet was then washed three times in 10 volumes of the same buffer without EGTA. Before the last centrifugation, the suspension of myofibrils was filtered through a stainless steel sieve with 0.25 mm meshes.

Myofibrils were kept in pellet overnight. Before use, the pellet was suspended in a small amount of buffer, the protein concentration was determined by the method of BRADFORD M., Anal. Biochem., 1976, 72, 248 and adjusted in order to have a concentration between 6 and 7 mg/ml.

(b) Myofibrillar ATPase activity

Ca++-dependent myfibrillar ATPase activity was determined at 21° C., pH 7.0, by measuring the rate of release of inorganic phosphate. All assays were performed within 24hrs. of final purification, using the method described by SOLARO and RUEGG, CIRC. RES., 51. 290–4,(1982). Reaction mixtures (4 ml) containing 0.6–0.7 mg/ml myofibrillar protein, 80mM KCl, 20 mM imidazole, 3 mM MgCl₂, 1 mM EGTA, the desired amount of CaCl₂, and the indicated concentration of drug or appropriate vehicle were preincubated for 6 min. prior to assay. The amount of $CaCl^2$ was varied between 0 and 0.9 mM and the pCa (-log free $Ca++$) computed using $2.514 \times 10^6 M^{-1}$ as the apparent affinity of $Ca++$ for EGTA at pH 7.0.

Reactions were initiated by the addition of $Na_2ATP$ to final concentration of 2 mM. After an incubation period of 12 min., reactions were quenched by the addition of an equal volume of ice-cold 10% trichloroacetic acid. The protein was pelleted by centrifugation (2000 g, 15 min.) and Pi was assayed in the supernatant fraction using a modification of the method described by LANZETTA et al, Anal. Biochem., 100, 95-97, (1979).

The following solutions were prepared:
(1) 3.7% ammonium heptamolybdate in 0.12 N $H_2SO_4$
(2) 0.074% malachite green oxalate in 1% polyvinylic alcohol.

The colour reagent was prepared by mixing an equal volume of solution (1) and (2) 15 min. before the assay. For the assay, 1,700 µl of 1% $H_2SO_4$ and 1 ml of colour reagent were added to 100 µl of sample. Colour development occurred at room temperature for 30 min. and was quenched by the addition of 200 µl of 1M tri-potassium citrate. The absorbance was measured at 620 millimicrons.

The effect of each compound, tested at the indicated concentration, on the relation between pCa and percent activation was determined taking 100% for the maximum ATPase activity obrained with vehicle alone. The effect on $Ca++$ sensitivity was quantified by measuring the shift of the pCa giving 50% of the maximal control ATPase activity.

The effect on maximal ATPase activity was expressed as the percent change of ATPase activity for pCa=5.47. Mean effects on myofibrillar ATPase activity were obtained from 1 to 5 preparations, (compounds tested at $2 \times 10^{-4}M$).

| | Results | | | |
|---|---|---|---|---|
| | CANINE CARDIAC PDE | | CANINE MYOFIBRIL ATPase | |
| Example No | CAM $IC_{50}$ (µM) | CGI $IC_{50}$ (µM) | 10 µM pCA/max | 30 µM pCA/max |
| 1 | 7.9 (n = 3) | 0.66 (n = 3) | 0.19 ± 0.09 +5 ± 0 | 0.25 ± 0.07 +1 ± 2 |
| 2 | 6.9 (n = 3) | 1.3 (n = 4) | 0.24 ± 0.01 +5 ± 2 | 0.60 ± 0.11 +13 ± 4 |
| 3 | >300 (n = 3) | 0.27 (n = 3) | — | +0.33 ± 0.05 +3 ± 3 |
| 4 | >300 (n = 3) | 0.44 (n = 3) | — | — |
| 5 | >>300 (n = 3) | 0.13 (n = 6) | — | — |
| 6 | >>300 (n = 3) | 1.2 (n = 3) | — | +0.38 ± 0.06 −2 ± 6 |
| 7 | 42.0 (n = 3) | 2.3 (n = 3) | — | +0.17 ± 0.02 −3 ± 5 |
| 8 | 19.0 (n = 3) | 1.20 (n = 3) | — | +0.87 ± 0.01 2 ± 3 |
| 9 | 31.0 (n = 3) | 2.10 (n = 3) | — | +0.05 ± 0.07 −20 ± 3 |
| 10 | 20.0 (n = 3) | 0.35 (n = 3) | — | +0.43 ± 0.07 −13 ± 3 |
| 11 | >>300 (n = 3) | 0.68 (n = 3) | — | +0.36 ± 0.05 8 ± 2 |
| 12 | — | 1.80 (n = 3) | — | +0.08 ± 0.02 −1 ± 2 |
| 13 | — | 14.0 (n = 3) | — | +0.07 ± 0.02 2 ± 2 |
| 14 | 5.6 (n = 3) | 0.62 (n = 3) | — | +0.12 ± 0.02 0 ± 3 |
| 15 | — | — | — | +0.08 ± 0.04 2 ± 4 |
| 16 | — | — | — | +0.17 ± 0.03 1 ± 4 |
| 17 | 23.0 (n = 3) | 0.43 (n = 3) | — | +0.60 ± 0.07 −16 ± 3 |
| 18 | 4.0 (n = 3) | 1.90 (n = 3) | — | +0.04 ± 0.08 −28 ± 4 |
| 19 | — | — | — | +0.23 ± 0.06 −14 ± 7 |
| 20 | — | — | — | +0.19 ± 0.08 −13 ± 5 |
| 21 | — | — | 1.07 ± 0.02 41 ± 2 | +1.30 ± 0.00 −42 ± 7 |
| 22 | — | — | — | +0.64 ± 0.1 21 ± 4 |
| 23 | — | — | — | +0.05 ± 0.02 8 ± 6 |
| 24 | — | — | — | +0.49 ± 0.06 −2 ± 5 |
| 25 | — | — | — | +0.49 ± 0.06 22 ± 3 |
| 26 | — | — | — | +0.65 ± 0.05 17 ± 2 |
| 27 | — | — | — | +0.05 ± 0.03 −1 ± 0 |

-continued

| Example No | Results CANINE CARDIAC PDE | | CANINE MYOFIBRIL ATPase | |
|---|---|---|---|---|
| | CAM IC$_{50}$ (μM) | CGI IC$_{50}$ (μM) | 10 μM pCA/max | 30 μM pCa/max |
| 28 | — | — | — | +0.94 ± 0.05 20 ± 5 |
| 29 | — | — | — | +0.78 ± 0.1 25 ± 4 |
| 30 | — | — | — | +1.01 ± 0.07 28 ± 6 |
| 31 | — | — | — | +0.43 ± 0.04 26 ± 7 |
| 32 | — | — | — | +0.10 ± 0.04 −1 ± 7 |
| 33 | — | — | — | +0.37 ± 0.05 3 ± 1 |
| 34 | — | — | — | +0.40 ± 0.02 5 ± 2 |
| 35 | — | — | — | +0.05 ± 0.06 0 ± 1 |
| 36 | — | — | — | +0.92 ± 0.06 24 ± 5 |
| 37 | — | — | — | +0.14 ± 0.03 −9 ± 1 |
| 38 | — | — | 1.10 ± 0.02 34 ± 7 | +1.05 ± 0.06 34 ± 5 |
| 39 | — | — | — | +0.04 ± 0.02 3 ± 2 |
| 41 | — | — | — | +0.11 ± 0.04 7 ± 2 |
| 42 | — | — | — | +0.30 ± 0.02 11 ± 4 |

2. Cardiotonic activity in the conscious instrumented dog.

Male Beagle dogs, at least 2 years old, weighing 12 to 18 kg were anaesthetised with pentobarbital sodium (30 mg/kg i.v.). Respiration was maintained by a Harward pump, model 613a. The heart was exposed through a left thoracotomy and a pericardial cradle was formed A high fidelity micromanometer (Koenigsberg P$_5$-P$_7$) was inserted into left ventricular lumen through a stab incision at the apex Wires were exteriorised to the back of the animals, placed into a size adapted jacket, and the chest closed. The experiments were conducted on the conscious dogs, 1 or 2 weeks after the surgery, when the animals had completely recovered.

Measured parameters were first derivative of left ventricular pressure, (dP/dt, mmHg/sec); heart rate (HR, beats/min.). A control period recording of 90 min. was made with the dogs placed in a quiet room, the recordings being made outside Compounds to be tested were administered orally in gelatin capsules and the parameters measured for 5 hrs. at least.

Results were expressed as the percentage of the maximum±SEM.

| Example No. | Dose mg/kg | Results ANAESTHETISED DOG-I.V. | | | |
|---|---|---|---|---|---|
| | | AoBP | H.R. | dP/dt Max | AoBF |
| 1 | 0.1 | +4 | +13 | +31 | +8 |
| | 0.3 | −9 | +30 | +54 | +16 |
| | 1.0 | −20 | +55 | 128 | +33 |
| 2 | 0.1 | +4 ± 2 | +13 ± 8 | +31 ± 9 | +8 ± 2 |
| | 0.3 | −9 ± 1 | +26 ± 10 | +54 ± 20 | +16 ± 1 |
| | 1.0 | −20 ± 5 | +55 ± 21 | +128 ± 56 | +33 ± 5 |
| 3 | 0.1 | −14 ± 7 | +28 ± 6 | +17 ± 6 | −30 ± 12 |
| | 0.3 | −29 ± 6 | +54 ± 11 | +70 ± 5 | −63 ± 8 |
| | 1.0 | −30 ± 1 | +93 ± 7 | +126 ± 9 | −50 ± 12 |
| 5 | 0.1 | −14 ± 6 | +8 ± 1 | +7 ± 2 | −25 ± 1 |

-continued

| Example No. | Dose mg/kg | Results ANAESTHETISED DOG-I.V. | | | |
|---|---|---|---|---|---|
| | | AoBP | H.R. | dP/dt Max | AoBF |
| | 0.3 | −12 ± 3 | +18 ± 7 | +24 ± 6 | −34 ± 5 |
| | 1.0 | −12 ± 1 | +19 ± 16 | +42 ± 16 | −28 ± 4 |
| | 3.0 | −19 ± 3 | +58 ± 0 | +116 ± 31 | −37 ± 2 |
| 17 | 0.3 | −8 ± 2 | +9 ± 3 | +6 ± 2 | +14 ± 2 |
| | 1.0 | −7 ± 1 | +22 ± 5 | +35 ± 8 | +16 ± 1 |
| | 3.0 | −20 ± 7 | +52 ± 13 | +81 ± 18 | +18 ± 4 |
| 31 | 0.01 | −8 ± 1 | +8 ± 2 | +9 ± 3 | +11 ± 5 |
| | 0.03 | −15 ± 1 | +30 ± 4 | +44 ± 13 | +19 ± 8 |
| | 0.1 | −23 ± 2 | +39 ± 6 | +93 ± 13 | +13 ± 6 |

We claim:

1. A compound of formula (I) or a pharmaceutically acceptable salt thereof,

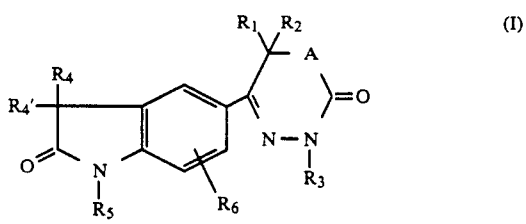

in which R$_1$ is hydrogen or lower alkyl; R$_2$ is hydrogen or lower alkyl; R$_4$ and R$_4'$ together form a group =N—Ra, or =CRaRb, where Ra is hydrogen, lower alkyl, aryl, aryloxy, lower alkylcarbonyl, arylcarbonyl, aryloxycarbonyl, lower alkoxy, lower alkoxy carbonyl, lower alkoxy carbonyl alkoxy, lower thioalkoxy, hydroxy, nitrile, pyridyl, thienyl, or imidazolyl, or —NRcRd, where Rc is hydrogen, lower alkyl, cycloalkyl, aryl, aralkyl, lower alkylcarbonyl, arylcarbonyl, aminocarbonyl, aminothiocarbonyl, aminoiminocarbonyl, lower alkoxycarbonyl, lower alkoxythiocarbonyl, aryloxycarbonyl, nitrile, carboxyl, pyridyl, thienyl or imidazolyl or heterocyclylcarbonyl wherein the heterocyclyl moiety is pyridyl, thienyl or imidazolyl, and Rd is hydrogen or lower alkyl; Rb is hydrogen, lower alkyl, aryl, lower alkylcarbonyl, lower alkoxycarbonyl, nitrile or nitro; or $R_4$ is —NH—Ra, in which Ra is as defined above, and $R_4$, is hydrogen or lower alkyl; each of $R_3$ and $R_5$ are hydrogen, lower alkyl, unsubstituted or substituted phenyl, lower alkylcarbonyl, unsubstituted or substituted phenylcarbonyl, unsubstituted or substituted pyridylcarbonyl, thienylcarbonyl or imidazoylcarbonyl, unsubstituted or substituted aminocarbonyl, lower alkoxycarbonyl or unsubstituted or substituted phenyloxycarbonyl, in which the substituents are one or more moieties selected from the group consisting of amino, nitro, hydroxy, lower alkyl, lower alkoxy, halogen, trifluoromethyl, lower alkyl sulphonyl and carboxyl; $R_6$ is hydrogen, lower alkyl or halogen; and A is sulphur; wherein aryl is an unsubstituted or substituted carbocyclic aromatic group having single or fused rings with 6 to 12 ring carbon atoms, the substituents selected from the group consistiong of amino, nitro, hydroxyl, lower alkyl, lower alkoxy, halogen, trifluoromethyl, lower alkyl sulphonyl and carboxyl.

2. A compound according to claim 1 in which each of $R_1, R_2, R_3, R_5$ and $R_6$ is independently hydrogen or $C_{1-6}$ alkyl.

3. A compound according to claim 1, in which aryl is phenyl unsubstituted or substituted by one or more moieties selected from the group consisting of amino, nitro, hydroxyl, alkyl of 1 to 6 carbon atoms, alkoxy of 1 to 6 carbon atoms, halogen, trifluoromethyl, alkyl sulphonyl of 1 to 6 carbon atoms in the alkyl moiety and carboxyl.

4. A compound selected from the group consisting of:
1,3-Dihydro-5-(3,6-dihydro-6-methyl-2-oxo-2H-1,3,4-thiadiazin-5-yl)-3-hydroxyimino-2H-indol-2-one;
1,3-Dihydro-5-(3,6-dihydro-6-methyl-2-oxo-2H-1,3,4 thiadiazin-5-yl)-3-methoxyimino-2H-indol-2-one;
O-Methyl 2-[2,3-dihydro-5-(3,6-dihydro-6-methyl-2-oxo -2H-1,3,4-thiadiazin-5-yl)-2-oxo-1H-indol-3-ylidene]-hydrazine carbothioate;
2-[2,3-Dihydro-5-(3,6-dihydro-6-methyl-2-oxo-2H-1,3,4-thiadiazin-5-yl)-2-oxo-1H-indol-3-ylidene]-hydrazine carbothioamide;
5-(3,6-Dihydro-6-methyl-2-oxo-2H-1,3,4-thiadiazin-5-yl)-1H-indole-2,3-dione 3-phenylhydrazone;
1,3-6-Dihydro-5-(3,6-dihydro-6-methyl-2-oxo-2H-1,3,4-thiadiazin-5-yl)-3-phenylimino-2H-indol-2-one;
5-(3,6-Dihydro-6-methyl-2-oxo-2H-1,3,4-thiadiazin-5-yl)-1H-indole-2,3-dione 3-hydrazone;
1,3-Dihydro-5-(3,6-dihydro-6-methyl-2-oxo-2H-1,3,4-thiadiazin-5-yl)-3-phenylamino-2H-indol-2-one, hydrochloride;
[5-(3,6-Dihydro-6-methyl-2-oxo-2H-1,3,4-thiadiazin-5-yl)-1,2-dihydro-2-oxo-3H-indol-3-ylidene]-propanedinitrile;
1,3,-Dihydro-5-(3,6-dihydro-6-methyl-2-oxo-2H-1,3,4-thiadiazin-5-yl)-3-phenylmethylene-2H-indol-2-one;
1,3,-Dihydro-5-(3,6-dihydro-6-methyl-2-oxo-2H-1,3,4-thiadiazin-5-yl)-3-phenoxyimino-2H-indol-2-one;
5-(3,6-Dihydro-6-methyl-2-oxo-2H-1,3,4-thiadiazin-5-yl)-1H-indole-2,3-dione 3-[2-(aminomethanimino) hydrazone];
5-(3,6-Dihydro-6-methyl-2-oxo-2H-1,3,4-thiadiazin-5-yl)-1H-indole-2,3-dione 3-[2-(4,5-dihydro-1H-2-imidazolyl)hydrazone];
1,3-Dihydro-5-(3,6-dihydro-6-methyl-2-oxo-2H-1,3,4-thiadiazin-5-yl)-3-(4-dimethylaminophenylimino)-2H -indol-2-one;
Methyl 2-[2,3-dihydro-5-(3,6-dihydro-6-methyl-2-oxo -2H-1,3,4-thiadiazin-5-yl)-2-oxo-1H-indol-3-ylidene]-hydrazine carboxylate;
1,3-Dihydro-5-(3,6-dihydro-6-methyl-2-oxo-2H-1,3,4-thiadiazin-5-yl)-3-(2-nitrophenylmethylene)-2H-indol -2-one;
1,3-Dihydro-5-(3,6-dihydro-6-methyl-2-oxo-2H-1,3,4-thiadiazin-5-yl)-3-[(2-hydroxyphenyl)methylene]-2H -indol-2-one;
1,3-Dihydro-5-(3,6-dihydro-6-methyl-2-oxo-2H-1,3,4-thiadiazin-5-yl)-3-(4-pyridylmethylene-2H-indol-2-one;
1,3-Dihydro-5-(3,6-dihydro-6-methyl-2-oxo-2H-1,3,4-thiadiazin-5-yl)-3-(3-pyridylmethylene)-2H-indol-2-one;
1,3-Dihydro-5-(3,6-dihydro-6-methyl-2-oxo-2H-1,3,4-thiadiazin-5-yl)-3-(2-pyridylmethylene)-2H-indol-2-one;
5-(3,6-Dihydro-6-methyl-2-oxo-2H-1,3,4-thiadiazin-5-yl)-1H-indole-2,3-dione 3-[(4-methyl)phenylhydrazone];
5-(3,6-Dihydro-6-methyl-2-oxo-2H-1,3,4-thiadiazin-5-yl)-1H-indole-2,3-dione 3-[(phenylmethyl)hydrazone];
Ethyl[[[2,3-dihydro-5-(3,6-dihydro-6-methyl-2-oxo-2H -1,3,4-thiadiazin-5-yl)-2-oxo-1H-indol-3-ylidene]amino]oxy]acetate;
5-(3,6-Dihydro-6-methyl-2-oxo-2H-1,3,4-thiadiazin-5-yl)-1H-indole-2,3-dione 3-[4-(1,1-dialethylethyl)-phenylhydrazone];
5-(3,6-Dihydro-6-methyl-2-oxo-2H-1,3,4-thiadiazin-5-yl)-1H-indole-2,3-dione 3-(cyclohexylhydrazone);
5-(3,6-Dihydro-6-methyl-2-oxo-2H-1,3,4-thiadiazin-5-yl)-1H-indole-2,3-dione 3-(methylphenylhydrazone);
5-(3,6-Dihydro-6-methyl-2-oxo-2H-1,3,4-thiadiazin-5-yl)-1H-indole-2,3-dione 3-[(3,4-dichlorophenyl)-hydrazone;
5-(3,6-Dihydro-6-methyl-2-oxo-2H-1,3,4-thiadiazin-5-yl)-1H-indole-2,3-dione 3-[(4-methoxy)phenylhydrazone];
5-(3,6-Dihydro-6-methyl-2-oxo-2H-1,3,4-thiadiazin-5-yl)-1H-indole-2,3-dione 3-[(4-chloro)phenylhydrazone];
5-(3,6-Dihydro-6-methyl-2-oxo-2H-1,3,4-thiadiazin-5-yl)-1H-indole-2,3-dione 3-[(4-fluoro)phenylhydrazone];
5-(3,6-Dihydro-6-methyl-2-oxo-2H-1,3,4-thiadiazin-5-yl)-1H-indole-2,3-dione 3-[(2-trifluoromethyl)-phenylhydrazone];
5-(3,6-Dihydro-6-methyl-2-oxo-2H-1,3,4-thiadiazin-5-yl)-1H-indole-2,3-dione 3-(pentafluorophenylhydrazone);
5-(3,6-Dihydro-6-methyl-2-oxo-2H-1,3,4-thiadiazin-5 -yl)-1H-indole-2,3-dione 3-[4-(methylsulfonyl)phenyl hydrazone]monoacetonitrile complex;

4-[2-[5-(3,6-Dihydro-6-methyl-2-oxo-2H-1,3,4-thiadiazin 5-yl)2,3-dihydro-2-oxo-1H-indol-3-ylidene]hydrazino]-benzoic acid;

5-(3,6-Dihydro-6-methyl-2-oxo-2H-1,3,4-thiadiazin-5-yl)-1H-indole-2,3-dione 3-(2-pyridylhydrazone) monohydrochloride;

5-(3,6-Dihydro-6-methyl-2-oxo-2H-1,3,4-thiadiazin-5-yl)-1H-indole-2,3-dione 3-(3-pyridylhydrazone);

2-Pyridinecarboxylic acid, 2-[2,3-dihydro-5-(3,6-dihydro-6-methyl-2-oxo-2H-1,3,4-thiadiazin-5-yl)-2-oxo -1H-indol-3-ylidene]hydrazide;

3-Pyridinecarboxylic acid, 2-[2,3-dihydro-5-(3,6-dihydro-6-methyl-2-oxo-2H-1,3,4-thiadiazin-5-yl)-2-oxo -1H-indol-3-ylidene]hydrazide hydrochloride;

4-Pyridinecarboxylic acid, 2-[2,3-dihydro-5-(3,6-dihydro-6-methyl-2-oxo-2H-1,3,4-thiadiazin-5-yl)-2-oxo -1H-indol-3-ylidene]hydrazide;

1,3-Dihydro-5-(3,6 dihydro-3,6-dimethyl-2-Oxo-2H-1,3,4-thiadiazin-5-yl)-3-phenylimino-2H-indol-2-one:

5-(3.6-Dihydro-3.6-dimethyl-2-oxo-2H-1,3,4-thiadiazin -5-yl)-1H-indole-2 3-dione 3-(phenylhydrazone);

5-(3.6-Dihydro-6-methyl-2-oxo-2H-1 3,4-thiadiazin-5-yl)-1H-indole-2 3-dione 3-[4-trifluoromethylphenyl-hydrazone];

2-Thiophenecarboxylic acid, 2-[2,3-dihydro-5-(3,6-dihydro-6-methyl-2-oxo-2H-1,3,4-thiadiazin-5-yl)-2-oxo-1H-indol-3-ylidene]hydrazide;

1,3-Dihydro-5-(3,6-dihydro-6-methyl-2-oxo-2H-1,3,4-one;

1,3-Dihydro-5-(3,6-dihydro-6-methyl-2-oxo-2H-1,3,4-thiadiazin-5-yl)-3-(3-thienylmethylene)-2H-indol-2-one.

5. A pharmaceutical composition comprising a compound of formula (I) as defined in claim 1, or a pharmaceutically acceptable salt thereof, and a pharmaceutically acceptable carrier.

6. A composition according to claim 5, in unit dosage form.

7. A method of treating congestive heart failure in mammals, which comprises administering an effective amount of a compound of formula (I) as defined in claim 1, or a pharmaceutically acceptable salt thereof, to the mammal.

* * * * *